US012644893B2

(12) United States Patent
Pennington et al.

(10) Patent No.: US 12,644,893 B2
(45) Date of Patent: Jun. 2, 2026

(54) METHOD OF DIAGNOSING OR PROGNOSING PSORIATIC ARTHRITIS

(71) Applicant: University College Dublin, Dublin (IE)

(72) Inventors: Stephen Pennington, County Clare (IE); Oliver Fitzgerald, Dublin (IE); Angela Mc Ardle, Dublin (IE)

(73) Assignee: University College Dublin, Dublin (IE)

( * ) Notice: Subject to any disclaimer, the term of this patent is extended or adjusted under 35 U.S.C. 154(b) by 783 days.

(21) Appl. No.: 17/265,181

(22) PCT Filed: Jul. 31, 2019

(86) PCT No.: PCT/EP2019/070719
§ 371 (c)(1),
(2) Date: Feb. 1, 2021

(87) PCT Pub. No.: WO2020/025721
PCT Pub. Date: Feb. 6, 2020

(65) Prior Publication Data
US 2021/0356476 A1      Nov. 18, 2021

(30) Foreign Application Priority Data
Aug. 1, 2018    (GB) ..................................... 1812571

(51) Int. Cl.
*G01N 33/68*          (2006.01)

(52) U.S. Cl.
CPC ... *G01N 33/6893* (2013.01); *G01N 2800/102* (2013.01)

(58) Field of Classification Search
CPC ..................... G01N 33/6893; G01N 2800/102
USPC ......................................................... 436/509
See application file for complete search history.

(56) References Cited

U.S. PATENT DOCUMENTS

| | | | |
|---|---|---|---|
| 2007/0184503 A1* | 8/2007 | Jemmerson .......... | G01N 33/566 |
| | | | 435/7.92 |
| 2016/0274106 A1* | 9/2016 | Kim ..................... | G01N 33/564 |
| 2018/0136220 A1* | 5/2018 | Grote ..................... | G16B 40/00 |

FOREIGN PATENT DOCUMENTS

| | | |
|---|---|---|
| WO | 2008063776 | 5/2008 |
| WO | 2008150494 | 12/2008 |

OTHER PUBLICATIONS

Cretu et al., Differentiating Psoriatic Arthritis From Psoriasis Without Psoriatic Arthritis Using Novel Serum Biomarkers, (2017), Arthritis Care & Research, vol. 70, No. 3, Mar. 2018, pp. 454-461. (Year: 2017).*
Ermel et al., Molecular Analysis of Rheumatoid Factors Derived From Rheumatoid Synovium Suggests an Antigen-Driven Response in Inflamed Joints, (1993), Arthritis and Rheumatism, vol. 36, No. 3 (Mar. 1993). (Year: 1993).*
Mc Ardle et al., Early biomarkers of joint damage in rheumatoid and psoriatic arthritis, (2015), Arthritis Research & Therapy (2015) 17:141. (Year: 2015).*
UniProtKB, A0N5G1, (2006), https://www.uniprot.org/uniprotkb/A0N5G1/entry. Retrieved on Jan. 8, 2024 at 16:55. (Year: 2006).*
UniProtKB, P02763, (1988), https://www.uniprot.org/uniprotkb/P02763/entry. Retrieved on Jan. 9, 2024 at 07:58. (Year: 1988).*
UNIPROTKB, P06396, (1988), https://www.uniprot.org/uniprotkb/P06396/entry. Retrieved on Jan. 9, 2024 at 08:10. (Year: 1988).*
Lubrano et al., Beyond TNF Inhibitors: New Pathways and Emerging Treatments for Psoriatic Arthritis, Drugs (2016) 76:663-673. (Year: 2016).*
Haringman et al., Synovial tissue macrophages: a sensitive biomarker for response to treatment in patients with rheumatoid arthritis, (2004), Ann Rheum Dis 2005;64:834-838. (Year: 2004).*
International Search Report and Written Opinion in corresponding PCT/EP2019/070719, dated Oct. 31, 2019.
Verheul, et al., "Biomarkers for rheumatoid and psoriatic arthritis", Clinical Immunology, 2015, 161(1) (abstract attached).
McArdle, et al., "Early biomarkers of joint damage in rheumatoid and psoriatic arthritis", Arthritis Research & Therapy, 2015, 17(141).
Office Action in co-pending Canadian Patent Application Serial No. 3,108,351, dated Nov. 1, 2023.
Office Action in co-pending Canadian Patent Application Serial No. 3,108,351, dated Jun. 5, 2024.

* cited by examiner

*Primary Examiner* — Gregory S Emch
*Assistant Examiner* — Omar Ramadan
(74) *Attorney, Agent, or Firm* — Hovey Williams LLP; Crissa A. Cook

(57) ABSTRACT

The present invention relates to methods of diagnosing or prognosing arthritis, specifically methods of diagnosing or prognosing psoriatic arthritis. Also disclosed are methods of diagnosing or prognosing rheumatoid arthritis, and methods of differentiating psoriatic arthritis from rheumatoid arthritis. Specifically, the methods involve determining the quantitative or qualitative level of one or more biomarkers in a biological sample from a subject.

14 Claims, 5 Drawing Sheets
Specification includes a Sequence Listing.

(A)

(B)

(C)

(D)

METHOD OF DIAGNOSING OR PROGNOSING PSORIATIC ARTHRITIS

CROSS-REFERENCE TO RELATED APPLICATIONS

The present application is the U.S. National Stage of International Patent Application No. PCT/EP2019/070719, filed Jul. 31, 2019, incorporated by reference in its entirety herein, which claims the priority benefit of Great Britain Application Serial No. 1812571.6, filed Aug. 1, 2018.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The present invention relates to methods of diagnosing or prognosing arthritis, specifically methods of diagnosing or prognosing psoriatic arthritis. Also disclosed are methods of diagnosing or prognosing rheumatoid arthritis, and methods of differentiating psoriatic arthritis from rheumatoid arthritis.

BACKGROUND TO THE INVENTION

Arthritis is a general term for conditions that affect the joints—the complex structures located where two or more bones meet. Despite this broad classification, there are more than 100 forms of arthritis, many of which can be grouped based on similar characteristics.

Rheumatoid Arthritis (RA) is the second most prevalent form of arthritis, affecting ~1% of the population. RA is classified as seropositive since rheumatoid factor (RF) is present in high titre in 80% of patients. Women are at a higher risk of developing RA compared to men, at a ratio of 2:1. RA is also associated with a strong genetic component—susceptibility has been linked to polymorphisms in the hypervariable region of Human leukocyte antigen (HLA)-DRβ1. RA is most prevalent in the small diarthridal joints of the hands and feet, but large joints (elbow, shoulder, hip, knee, ankles) can also be affected, and the pattern of joint involvement is typically symmetrical. RA 35 is a debilitating disease, whereby joint damage leads to pain and disability, and up to one third of patients become work disabled 2 years after onset.

Psoriatic Arthritis (PsA) can be defined as arthritis with psoriasis (Ps), predominantly Ps vulgaris (a form of plaque Ps). Usually negative for RF (seronegative), PsA is characterised radiographically by both bone resorption and peri-articular new bone formation. PsA is a form of inflammatory arthritis (IA), affecting approximately 0.25% of the population. It is a heterogeneous disorder associated with joint damage, disability, disfiguring skin disease and, in severe cases, mortality. Inherently irreversible and frequently progressive, the process of joint damage begins at, or before, the clinical onset of disease. Early recognition and intervention is thus crucial to patient outcome.

PsA is most often diagnosed by history and physical examination, and onset of disease is clinically recognised when a patient presents with musculoskeletal inflammation, presence of psoriasis, and an absence of rheumatoid factor. Currently there are no diagnostic criteria for PsA, and recognition of the disease is dependent on the expertise of the treating clinician. Therefore, the diagnosis of PsA is often missed or delayed and this has been associated with functional consequences for the patient. From a rheumatologists perspective, at disease onset, PsA is particularly difficult to distinguish from other forms of arthritis, especially RA (as both can present with peripheral arthritis and Ps).

In the context of PsA and RA, making an accurate diagnosis is not the only challenge faced by rheumatologists—despite the similarities between PsA and RA, their distinctive pathologies require different treatments. For example, drugs that are effective in RA may not be effective in PsA and can even cause adverse effects. For instance, while there are some medications which are effective for both PsA and RA (e.g. methotrexate; or anti-TNFα inhibitors), there are others which would be best avoided in PsA because of adverse effects (e.g. hydroxychloroquine, or corticosteroid), some which have proven efficacy in RA and not PsA (e.g. rituximab, or tocilizumab) and some with proven efficacy in PsA and not in RA (e.g. ustekinumab, apremilast, or anti-IL17 therapies). Evidence suggests that the early introduction of the appropriate, effective medication would result in better short-term and long-term patient outcomes. When a patient presents with PsA, a number of treatment options become available. Currently, the therapeutic strategy follows a period of trial and error, since many patients do not respond, cannot tolerate, or remit upon cessation of any given therapy. For the patient, several months may be lost as a result of trial and error testing—meanwhile irreversible joint damage may occur.

Clearly more effective clinical tests are urgently needed to improve personalized patient care in PsA. Specifically there is need to develop minimally invasive tests predictive of diagnosis that would allow for early intervention. Such a diagnostic test in PsA would facilitate early detection and therapeutic intervention. This in turn would have a positive impact on patient outcome and relieve both individual suffers and society from a substantial financial burden. Finally, it is likely that such a test would improve the reliability of data from epidemiological studies and intervention trials and therefore enhance research in PsA.

SUMMARY OF THE INVENTION

According to a first aspect of the present invention, there is provided a method of diagnosing or prognosing psoriatic arthritis in a subject, the method comprising the steps of:

(a) determining the quantitative or qualitative level of one or more biomarkers in a biological sample from the subject; and (b) diagnosing or prognosing psoriatic arthritis in the subject based on the quantitative or qualitative level of the or each biomarker in the biological sample;

wherein the or each biomarker is selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; and Thrombospondin-1.

Optionally or additionally, the or each biomarker is selected from: Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1;

Lipopolysaccharide-binding protein; Pigment epithelium-derived factor; Vitamin K-dependent protein C; and Prothrombin.

Optionally, the or each biomarker is selected from: Rheumatoid factor C6 light chain; Leucine-rich alpha-2-glyco-protein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

Optionally or additionally, the or each biomarker is selected from: Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the or each biomarker is selected from: Rheumatoid factor C6 light chain; Leucine-rich alpha-2-glyco-protein; Alpha-1-antichymotrypsin; Complement C4-B; Coagulation factor XI; Haptoglobin; Haptoglobin-related protein; Thrombospondin-1; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glyco-protein chain B; and Antithrombin-III.

Optionally, the or each biomarker is selected from: Rheumatoid factor C6 light chain; Leucine-rich alpha-2-glyco-protein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; Prothrombin; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

According to a second aspect of the present invention, there is provided a method of diagnosing or prognosing rheumatoid arthritis in a subject, the method comprising the steps of:
   (a) determining the quantitative or qualitative level of one or more biomarkers in a biological sample from the subject; and
   (b) diagnosing or prognosing rheumatoid arthritis in the subject based on the quantitative or qualitative level of the or each biomarker in the biological sample;

wherein the or each biomarker is selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; and Thrombospondin-1.

Optionally or additionally, the or each biomarker is selected from: Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

Optionally, the or each biomarker is selected from: Rheumatoid factor C6 light chain; Leucine-rich alpha-2-glyco-protein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

Optionally or additionally, the or each biomarker is selected from: Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the or each biomarker is selected from: Rheumatoid factor C6 light chain; Leucine-rich alpha-2-glyco-protein; Alpha-1-antichymotrypsin; Complement C4-B; Coagulation factor XI; Haptoglobin; Haptoglobin-related protein; Thrombospondin-1; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glyco-protein chain B; and Antithrombin-III.

Optionally, the or each biomarker is selected from: Rheumatoid factor C6 light chain; Leucine-rich alpha-2-glyco-protein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; Prothrombin; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3;

Insulin-like growth factor-binding protein 3; Galectin-3-binding protein; Alpha-2-HS-glycoprotein chain B; and Antithrombin-III.

According to a third aspect of the present invention, there is provided a method of differentiating psoriatic arthritis from rheumatoid arthritis in a subject, the method comprising the steps of:

(a) determining the quantitative or qualitative level of one or more biomarkers in a biological sample from the subject; and (b) differentiating psoriatic arthritis from rheumatoid arthritis in the subject based on the quantitative or qualitative level of the or each biomarker in the biological sample;

wherein the or each biomarker is selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; and Thrombospondin-1.

Optionally or additionally, the or each biomarker is selected from: Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

Optionally, the or each biomarker is selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

Optionally or additionally, the or each biomarker is selected from: Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the or each biomarker is selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; Thrombospondin-1; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the or each biomarker is selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; Prothrombin; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the method of differentiating psoriatic arthritis from rheumatoid arthritis in a subject comprises differentiating subjects suffering from psoriatic arthritis from subjects suffering from rheumatoid arthritis based on the quantitative or qualitative level of the or each biomarker in the biological sample.

Optionally, the determining step (a) comprises determining the quantitative or qualitative level of two or more biomarkers in the biological sample from the subject.

Further optionally, the determining step (a) comprises determining the quantitative or qualitative level of three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one biomarkers in the biological sample from the subject.

Optionally, the determining step (a) comprises determining the quantitative or qualitative level of all of the biomarkers in the biological sample from the subject.

Optionally or additionally, the determining step (a) comprises determining the quantitative or qualitative level of each of the biomarkers in the biological sample from the subject.

Optionally, the or each biomarker is a gene. Further optionally, the or each biomarker is a nucleic acid. Still further optionally, the or each biomarker is a deoxyribonucleic acid. Alternatively, the or each biomarker is a ribonucleic acid.

Optionally, the or each biomarker is a gene selected from: V-kappa-1; LRG1; AACT; C4B; F11; HP; HPR; and THBS1.

Optionally or additionally, the or each biomarker is a gene selected from: ORM1; SERPINA1; AACT; IGFALS; AT3; C4BPA; CP; CFB; CLU; PPBP; ECM1; ITIH4; KNG1; LBP; SERPINF1; PROC; and F2.

Optionally, the or each biomarker is a gene selected from: V-kappa-1; LRG1; AACT; C4B; F11; HP; HPR; THBS1; ORM1; SERPINA1; AACT; IGFALS; AT3; C4BPA; CP; CFB; CLU; PPBP; ECM1; ITIH4; KNG1; LBP; SERPINF1; PROC; and F2.

Optionally or additionally, the or each biomarker is a gene selected from: GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a gene selected from: V-kappa-1; LRG1; AACT; C4B; F11; HP; HPR; THBS1;

GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a gene selected from: V-kappa-1; LRG1; AACT; C4B; F11; HP; HPR; THBS1; ORM1; SERPINA1; AACT; IGFALS; AT3; C4BPA; CP; CFB; CLU; PPBP; ECM1; ITIH4; KNG1; LBP; SERPINF1; PROC; F2; GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a nucleic acid defined by a Genbank Accession/Version Number selected from: S56182.1; NM_052972.2; K01500.1; NM_001002029.3; NM_000128.3; NM_005143.4; NM_020995.3; and NM_003246.3.

Optionally or additionally, the or each biomarker is a nucleic acid defined by a Genbank Accession/Version Number selected from: NM_000607.2; NM_001002235.2; NM_001146006.1; AB083701.1; NM_000715.3; NM_000096.3; NM_001710.5; NM_001831.3; NM_002704.3; NM_004425.3; NM_002218.4; and NM_003246.3.

Optionally, the or each biomarker is a nucleic acid defined by a Genbank Accession/Version Number selected from: S56182.1; NM_052972.2; K01500.1; NM_001002029.3; NM_000128.3; NM_005143.4; NM_020995.3; NM_003246.3; NM_000607.2; NM_001002235.2; NM_001146006.1; AB083701.1; NM_000715.3; NM_000096.3; NM_001710.5; NM_001831.3; NM_002704.3; NM_004425.3; NM_002218.4; and NM_003246.3.

Optionally or additionally, the or each biomarker is a nucleic acid defined by a Genbank Accession/Version Number selected from: NM_000177.5; NM_001127487.2; NM_001737.5; NM_005809.6; NM_000062.2; NM_000624.6; NM_002864.3; NM_001002810.3; NM_001647.4; NM_000173.7; NM_001133.2; NM_002217.3; NM_005567.4; NM_001622.4; and NM_000488.3.

Optionally, the or each biomarker is a nucleic acid defined by a Genbank Accession/Version Number selected from: S56182.1; NM_052972.2; K01500.1; NM_001002029.3; NM_000128.3; NM_005143.4; NM_020995.3; NM_003246.3; NM_000177.5; NM_001127487.2; NM_001737.5; NM_005809.6; NM_000062.2; NM_000624.6; NM_002864.3; NM_001002810.3; NM_001647.4; NM_000173.7; NM_002217.3; NM_005567.4; NM_001622.4; and NM_000488.3.

Optionally or additionally, the or each biomarker is a nucleic acid defined by a Genbank Accession/Version Number selected from: S56182.1; NM_052972.2; K01500.1; NM_001002029.3; NM_000128.3; NM_005143.4; NM_020995.3; NM_003246.3; NM_000607.2; NM_001002235.2; NM_001146006.1; AB083701.1; NM_000715.3; NM_000096.3; NM_001710.5; NM_001831.3; NM_002704.3; NM_004425.3; NM_002218.4; and NM_003246.3; NM_000177.5; NM_001127487.2; NM_001737.5; NM_005809.6; NM_000062.2; NM_000624.6; NM_002864.3; NM_001002810.3; NM_001647.4; NM_000173.7; NM_001133.2; NM_002217.3; NM_005567.4; NM_001622.4; and NM_000488.3.

Optionally, the or each biomarker is a translation product of a gene.

Optionally, the or each biomarker is a translation product of a gene selected from: V-kappa-1; LRG1; AACT; C4B; F11; HP; HPR; and THBS1.

Optionally or additionally, the or each biomarker is a translation product of a gene selected from: ORM1; SERPINA1; AACT; IGFALS; AT3; C4BPA; CP; CFB; CLU; PPBP; ECM1; ITIH4; KNG1; LBP; SERPINF1; PROC; and F2.

Optionally, the or each biomarker is a translation product of a gene selected from: V-kappa-1; LRG1; AACT; C4B; F11; HP; HPR; THBS1; ORM1; SERPINA1; AACT; IGFALS; AT3; C4BPA; CP; CFB; CLU; PPBP; ECM1; ITIH4; KNG1; LBP; SERPINF1; PROC; and F2.

Optionally or additionally, the or each biomarker is a translation product of a gene selected from: GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a translation product of a gene selected from: V-kappa-1; LRG1; AACT; C4B; F11; HP; HPR; THBS1; GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a translation product of a gene selected from: V-kappa-1; LRG1; AACT; C4B; F11; HP; HPR; THBS1; ORM1; SERPINA1; AACT; IGFALS; AT3; C4BPA; CP; CFB; CLU; PPBP; ECM1; ITIH4; KNG1; LBP; SERPINF1; PROC; F2; GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a translation product of a nucleic acid defined by a Genbank Accession/Version Number selected from: S56182.1; NM_052972.2; K01500.1; NM_001002029.3; NM_000128.3; NM_005143.4; NM_020995.3; and NM_003246.3.

Optionally, the or each biomarker is a translation product of a nucleic acid defined by a Genbank Accession/Version Number selected from: NM_000607.2; NM_001002235.2; NM_001146006.1; AB083701.1; NM_000715.3; NM_000096.3; NM_001710.5; NM_001831.3; NM_002704.3; NM_004425.3; NM_002218.4; and NM_003246.3.

Optionally, the or each biomarker is a translation product of a nucleic acid defined by a Genbank Accession/Version Number selected from: S56182.1; NM_052972.2; K01500.1; NM_001002029.3; NM_000128.3; NM_005143.4; NM_020995.3; NM_003246.3; NM_000607.2; NM_001002235.2; NM_001146006.1; AB083701.1; NM_000715.3; NM_000096.3; NM_001710.5; NM_001831.3; NM_002704.3; NM_004425.3; NM_002218.4; and NM_003246.3.

Optionally or additionally, the or each biomarker is a translation product of a nucleic acid defined by a Genbank Accession/Version Number selected from: NM_000177.5; NM_001127487.2; NM_001737.5; NM_005809.6: NM 000062.2: NM_000624.6; NM 002864.3: NM_001002810.3; NM_001647.4; NM_000173.7; NM_001133.2; NM_002217.3; NM_005567.4; NM_001622.4; and NM_000488.3.

Optionally, the or each biomarker is a translation product of a nucleic acid defined by a Genbank Accession/Version Number selected from: S56182.1; NM_052972.2; K01500.1; NM_001002029.3; NM_000128.3; NM_005143.4; NM_020995.3; NM_003246.3; NM_000177.5; NM_001127487.2; NM_001737.5; NM_005809.6; NM_000062.2; NM_000624.6;

NM_002864.3; NM_001002810.3; NM_001647.4; NM_000173.7; NM_001133.2; NM_002217.3; NM_005567.4; NM_001622.4; and NM_000488.3.

Optionally or additionally, the or each biomarker is a translation product of a nucleic acid defined by a Genbank Accession/Version Number selected from: S56182.1; NM_052972.2; K01500.1; NM_001002029.3; NM_000128.3; NM_005143.4; NM_020995.3; NM_003246.3; NM_000607.2; NM_001002235.2; NM_001146006.1; AB083701.1; NM_000715.3; NM_000096.3; NM_001710.5; NM_001831.3; NM_002704.3; NM_004425.3; NM_002218.4; and NM_003246.3; NM_000177.5; NM_001127487.2; NM_001737.5; NM_005809.6; NM_000062.2; NM_000624.6; NM_002864.3; NM_001002810.3; NM_001647.4; NM_000173.7; NM_001133.2; NM_002217.3; NM_005567.4; NM_001622.4; and NM_000488.3.

Optionally, the or each biomarker is a protein. Further optionally, the or each biomarker is a peptide. Still further optionally, the or each biomarker is a polypeptide.

Optionally, the or each biomarker is a protein encoded by a gene selected from: V-kappa-1; LRG1; AACT; C4B; F11; HP; HPR; and THBS1.

Optionally or additionally, the or each biomarker is a protein encoded by a gene selected from: ORM1; SER-PINA1; AACT; IGFALS; AT3; C4BPA; CP; CFB; CLU; PPBP; ECM1; ITIH4; KNG1; LBP; SERPINF1; PROC; and F2.

Optionally, the or each biomarker is a protein encoded by a gene selected from: V-kappa-1; LRG1; AACT; C4B; F11; HP; HPR; THBS1; ORM1; SERPINA1; AACT; IGFALS; AT3; C4BPA; CP; CFB; CLU; PPBP; ECM1; ITIH4; KNG1; LBP; SERPINF1; PROC; and F2.

Optionally or additionally, the or each biomarker is a protein encoded by a gene selected from: GSN, FLNC, C9, PRDX2, SERPING1, SERPINA5, PZP, PDE4DIP, APOD, GP1BA, AFM, ITIH3, LGALS3BP, AHSG, and SER-PINC1.

Optionally, the or each biomarker is a protein encoded by a gene selected from: V-kappa-1; LRG1; AACT; C4B; F11; HP; HPR; THBS1; GSN, FLNC, C9, PRDX2, SERPING1, SERPINA5, PZP, PDE4DIP, APOD, GP1BA, AFM, ITIH3, LGALS3BP, AHSG, and SERPINC1.

Optionally, the or each biomarker is a protein encoded by a gene selected from: V-kappa-1; LRG1; AACT; C4B; F11; HP; HPR; THBS1; ORM1; SERPINA1; AACT; IGFALS; AT3; C4BPA; CP; CFB; CLU; PPBP; ECM1; ITIH4; KNG1; LBP; SERPINF1; PROC; F2; GSN, FLNC, C9, PRDX2, SERPING1, SERPINA5, PZP, PDE4DIP, APOD, GP1BA, AFM, ITIH3, LGALS3BP, AHSG, and SER-PINC1.

Optionally, the or each biomarker is a protein selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; and Thrombospondin-1.

Optionally or additionally, the or each biomarker is a protein selected from: Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Pro-thrombin.

Optionally, the or each biomarker is a protein selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; Thrombospondin-1; Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

Optionally or additionally, the or each biomarker is a protein selected from: Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the or each biomarker is a protein selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; Thrombospondin-1; Gelsolin; Filamin-C; Complement component C9b; Peroxiredoxin-2; Plasma ser-ine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glyco-protein chain B; and Antithrombin-III.

Optionally, the or each biomarker is a protein selected from: Rheumatoid factor C6 light chain; Leucine-rich alpha-2-glycoprotein; Alpha-1-antichymotrypsin; Complement C4-B; Coagulation factor XI; Haptoglobin; Haptoglobin-related protein; Thrombospondin-1; Alpha-1-acid glycopro-tein 1; Alpha-1-antitrypsin; Insulin-like growth factor-bind-ing protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pig-ment epithelium-derived factor; Vitamin K-dependent pro-tein C; Prothrombin; Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

Optionally, the or each biomarker is a protein defined by a UniProt Accession Number selected from: A0N5G1; P02750; P01011; P0C0L5; P03951; P00738; P00739; and P07996.

Optionally or additionally, the or each biomarker is a protein defined by a UniProt Accession Number selected from: P02763; P01009; P35858; Q8J001; P04003; P00450; P00751; P10909; P02775; Q16610; Q14624; P01042; P18428; P36955; P04070; and P00734.

Optionally, the or each biomarker is a protein defined by a UniProt Accession Number selected from: A0N5G1; P02750; P01011; P0C0L5; P03951; P00738; P00739; P07996; P02763; P01009; P35858; Q8J001; P04003;

P00450; P00751; P10909; P02775; Q16610; Q14624; P01042; P18428; P36955; P04070; and P00734.

Optionally or additionally, the or each biomarker is a protein defined by a UniProt Accession Number selected from: P06396; Q14315; P32119; P05155; P05154; P02748; P20742; Q5VU43; P05090; P07359; P43652; Q06033; Q08380; P02765; and P01008.

Optionally, the or each biomarker is a protein defined by a UniProt Accession Number selected from: A0N5G1; P02750; P01011; P0C0L5; P03951; P00738; P00739; P07996; P06396; Q14315; P02748; P32119; P05155; P05154; P02748; P20742; Q5VU43; P05090; P07359; P43652; P05155; Q06033; Q08380; P02765; and P01008.

Optionally, the or each biomarker is a protein defined by a UniProt Accession Number selected from: A0N5G1; P02750; P01011; P0C0L5; P03951; P00738; P00739; P07996; P02763; P01009; P35858; Q8J001; P04003; P00450; P00751; P10909; P02775; Q16610; Q14624; P01042; P18428; P36955; P04070; P00734; P06396; Q14315; P32119; P05155; P05154; P02748; P20742; Q5VU43; P05090; P07359; P43652; Q06033; Q08380; P02765; and P01008.

Optionally, the or each biomarker is a protein defined by a Genbank Accession/Version Number selected from: AAB25742.1; NP_443204.1; K01500.1; NP_001002029.3; NP_000119.1; NP_005134.1; NP_066275.3; and NP_003237.2.

Optionally or additionally, the or each biomarker is a protein defined by a Genbank AccessionVersion Number selected from: NP_000598.2; NP_001002235.1; NP_001139478.1; BAC21173.1; NP_000706.1; NP_000087.1; NP_001701.2; NP_001822.3; NP_002695.1; NP_004416.2; NP_002209.2; NP_001095886.1; NP_004130.2; NP_002606.3; NP_000303.1; and NP_000497.1.

Optionally, the or each biomarker is a protein defined by a Genbank Accession/Version Number selected from: AAB25742.1; NP_443204.1; K01500.1; NP_001002029.3; NP_000119.1; NP_005134.1; NP_066275.3; NP_003237.2; NP_000598.2; NP_001002235.1; NP_001139478.1; BAC21173.1; NP_000706.1; NP_000087.1; NP_001701.2; NP_001822.3; NP_002695.1; NP_004416.2; NP_002209.2; NP_001095886.1; NP_004130.2; NP_002606.3; NP_000303.1; and NP_000497.1.

Optionally or additionally, the or each biomarker is a protein defined by a Genbank AccessionVersion Number selected from: NP_000168.1; NP_001120959.1; NP_001728.1; NP_005800.3; NP_000053.2; NP_000615.3; NP_002855.2; NP_001002810.1; NP_001638.1; NP_000164.5; NP_001124.1; NP_002208.3; NP_005558.1; NP_001613.2; and NP_000479.1.

Optionally, the or each biomarker is a protein defined by a Genbank Accession/Version Number selected from: AAB25742.1; NP_443204.1; K01500.1; NP_001002029.3; NP_000119.1; NP_005134.1; NP_066275.3; NP_003237.2; NP_000168.1; NP_001120959.1; NP_001728.1; NP_005800.3; NP_000053.2; NP_000615.3; NP_002855.2; NP_001002810.1; NP_001638.1; NP_000164.5; NP_001124.1; NP_002208.3; NP_005558.1; NP_001613.2; and NP_000479.1.

Optionally, the or each biomarker is a protein defined by a Genbank Accession/Version Number selected from: AAB25742.1; NP_443204.1; K01500.1; NP_001002029.3; NP_000119.1; NP_005134.1; NP_066275.3; NP_003237.2; NP_000598.2; NP_001002235.1; NP_001139478.1; BAC21173.1; NP_000706.1; NP_000087.1; NP_001701.2; NP_001822.3; NP_002695.1;

NP_004416.2; NP_002209.2; NP_001095886.1; NP_004130.2; NP_002606.3; NP_000303.1; NP_000497.1; NP_000168.1; NP_001120959.1; NP_001728.1; NP_005800.3; NP_000053.2; NP_000615.3; NP_002855.2; NP_001002810.1; NP_001638.1; NP_000164.5; NP_001124.1; NP_002208.3; NP_005558.1; NP_001613.2; and NP_000479.1.

Optionally, the or each biomarker is a protein comprising an amino acid sequence selected from any one of SEQ ID NOs: 1-18.

Optionally or additionally, the or each biomarker is a protein having an amino acid sequence selected from any one of SEQ ID NOs: 19-37.

Optionally, the or each biomarker is a protein comprising an amino acid sequence selected from any one of SEQ ID NOs: 1-37.

Optionally or additionally, the or each biomarker is a protein having an amino acid sequence selected from any one of SEQ ID NOs: 38-55.

Optionally, the or each biomarker is a protein comprising an amino acid sequence selected from any one of SEQ ID NOs: 1-55.

Optionally, the determining step (a) comprises determining the quantitative or qualitative level of one or more subsets of one or more biomarkers in the biological sample from the subject.

Optionally, the determining step (a) comprises determining the quantitative or qualitative level of two or more subsets of one or more biomarkers in the biological sample from the subject.

Optionally, the determining step (a) comprises determining the quantitative or qualitative level of one or more of a first or second subset of one or more biomarkers in the biological sample from the subject.

Optionally, the determining step (a) comprises determining the quantitative or qualitative level of a first and second subset of one or more biomarkers in the biological sample from the subject.

Optionally, the first subset comprises one or more biomarkers selected from: Complement C4-B; Extracellular matrix protein 1; Coagulation factor XI; Pigment epithelium-derived factor; and Prothrombin.

Optionally, the second subset comprises one or more biomarkers selected from: Rheumatoid factor C6 light chain; Alpha-1-acid glycoprotein 1; Alpha-1-antitrypsin; Leucine-rich alpha-2-glycoprotein; alpha-1-antichymotrypsin; Ceruloplasmin; Haptoglobin; Haptoglobin-related protein; Inter-alpha-trypsin inhibitor heavy chain H4; Lipopolysaccharide-binding protein; and Thrombospondin-1.

Optionally, the first and second subset comprise one or more biomarkers selected from: Complement C4-B; Extracellular matrix protein 1; Coagulation factor XI; Pigment epithelium-derived factor; Prothrombin; Rheumatoid factor C6 light chain; Alpha-1-acid glycoprotein 1; Alpha-1-antitrypsin; Leucine-rich alpha-2-glycoprotein; alpha-1-antichymotrypsin; Ceruloplasmin; Haptoglobin; Haptoglobin-related protein; Inter-alpha-trypsin inhibitor heavy chain H4; Lipopolysaccharide-binding protein; and Thrombospondin-1.

Optionally, the diagnosing or prognosing step (b) comprises comparing the quantitative or qualitative level of the or each biomarker in the biological sample from the subject with the quantitative or qualitative level of the or each respective biomarker in a normal sample.

Optionally, the differentiating step (b) comprises comparing the quantitative or qualitative level of the or each biomarker in the biological sample from the subject with the quantitative or qualitative level of the or each respective biomarker in a normal sample.

Optionally, the normal sample is a biological sample from a subject not suffering from psoriatic arthritis. Optionally or additionally, the normal sample is a biological sample from a subject not suffering from rheumatoid arthritis.

Optionally, a quantitative or qualitative level of the or each biomarker in the biological sample from the subject greater than the quantitative or qualitative level of the or each respective biomarker in a normal sample is indicative of the quantitative or qualitative level of psoriatic arthritis.

Optionally, a quantitative or qualitative level of the or each biomarker in the biological sample from the subject greater than the quantitative or qualitative level of the or each respective biomarker in a normal sample is indicative of the quantitative or qualitative presence of rheumatoid arthritis.

Optionally, the determining step (a) comprises determining the quantitative or qualitative level of all of the biomarkers in one or more of the first or second subsets.

Optionally, the determining step (a) comprises determining the quantitative or qualitative level of each of the biomarkers in one or more of the first or second subsets.

Optionally, the determining step (a) comprises determining the quantitative or qualitative level of each of the biomarkers in the first and second subsets.

Optionally, the diagnosing or prognosing step (b) comprises comparing the quantitative or qualitative level of the or each biomarker in the or each subset in the biological sample from the subject with the quantitative or qualitative level of the or each respective biomarker in a normal sample.

Optionally, a quantitative or qualitative level of the or each biomarker in the or each subset in the biological sample from the subject greater than the quantitative or qualitative level of the or each respective biomarker in a normal sample is indicative of the quantitative or qualitative level of psoriatic arthritis.

Optionally, a quantitative or qualitative level of the or each biomarker in the or each subset in the biological sample from the subject greater than the quantitative or qualitative level of the or each respective biomarker in a normal sample is indicative of the quantitative or qualitative presence of rheumatoid arthritis.

Optionally, the differentiating step (b) comprises comparing the quantitative or qualitative level of the or each biomarker in the biological sample from the subject with the quantitative or qualitative level of the or each respective biomarker in a normal sample.

Optionally, the differentiating step (b) comprises comparing the quantitative or qualitative level of the or each biomarker in the or each subset in the biological sample from the subject with the quantitative or qualitative level of the or each respective biomarker in another subset in the biological sample.

Optionally, the differentiating step (b) comprises comparing the quantitative or qualitative level of the or each biomarker in a first subset in the biological sample from the subject with the quantitative or qualitative level of the or each respective biomarker in another subset in the biological sample.

Optionally, the differentiating step (b) comprises comparing the quantitative or qualitative level of the or each biomarker in a first subset in the biological sample from the subject with the quantitative or qualitative level of the or each biomarker in a second subset in the biological sample.

Optionally, a quantitative or qualitative level of the or each biomarker in the or each subset in the biological sample from the subject greater than the quantitative or qualitative level of the or each biomarker in another subset in the biological sample is indicative of the quantitative or qualitative level of psoriatic arthritis.

Optionally, a quantitative or qualitative level of the or each biomarker in the first subset in the biological sample from the subject greater than the quantitative or qualitative level of the or each biomarker in the second subset in the biological sample is indicative of the quantitative or qualitative presence of psoriatic arthritis.

Optionally, a quantitative or qualitative level of the or each biomarker in the first subset in the biological sample from the subject less than the quantitative or qualitative level of the or each biomarker in the second subset in the biological sample is indicative of the quantitative or qualitative presence of rheumatoid arthritis.

Optionally, the biological sample is selected from whole blood, serum, plasma, urine, interstitial fluid, peritoneal fluid, tears, saliva, buccal swab, skin, synovial fluid, synovium, and cerebrospinal fluid.

The term "prognosing" is intended to define the usual medical step of prognosis, and is intended to also include predicting a defined outcome, such as a defined medical outcome, including predicting a prospect of: a disease-free outcome, such as recovery an improvement in disease, such as a reduction in symptom; likelihood of survival, such as life expectancy; and change in disease state, such as progression.

BRIEF DESCRIPTION OF THE DRAWINGS

Embodiments of the present invention will now be described with reference to the following non-limiting examples and accompanying drawings, in which.

EXAMPLES

Materials and Methods

Patients

Figure 1:
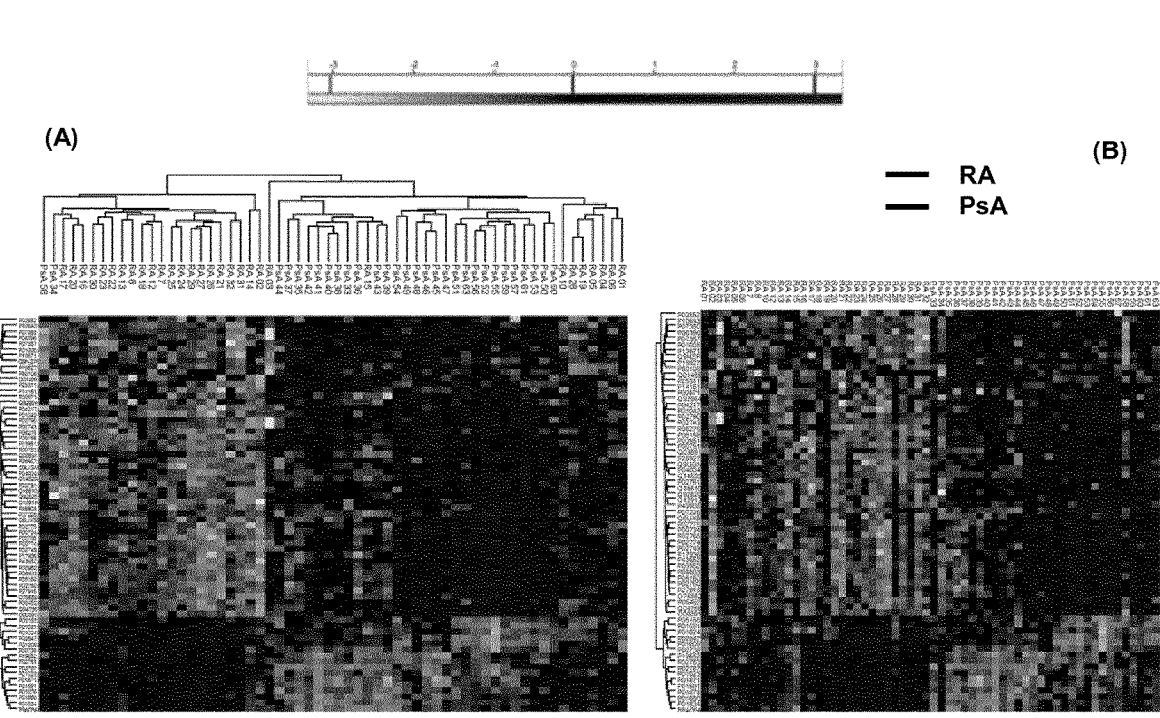
FIG. 1 illustrates the association of protein signatures with diagnosis as shown by (A) unsupervised hierarchical cluster analysis (HCA), (B) supervised HCA and (C) Principal component analysis, wherein plots were generated on differentially expressed proteins between PsA (n=30) and RA (n=30) patients ($p \leq 0.01$, Benjamini Hochberg FDR)
Figure 1:
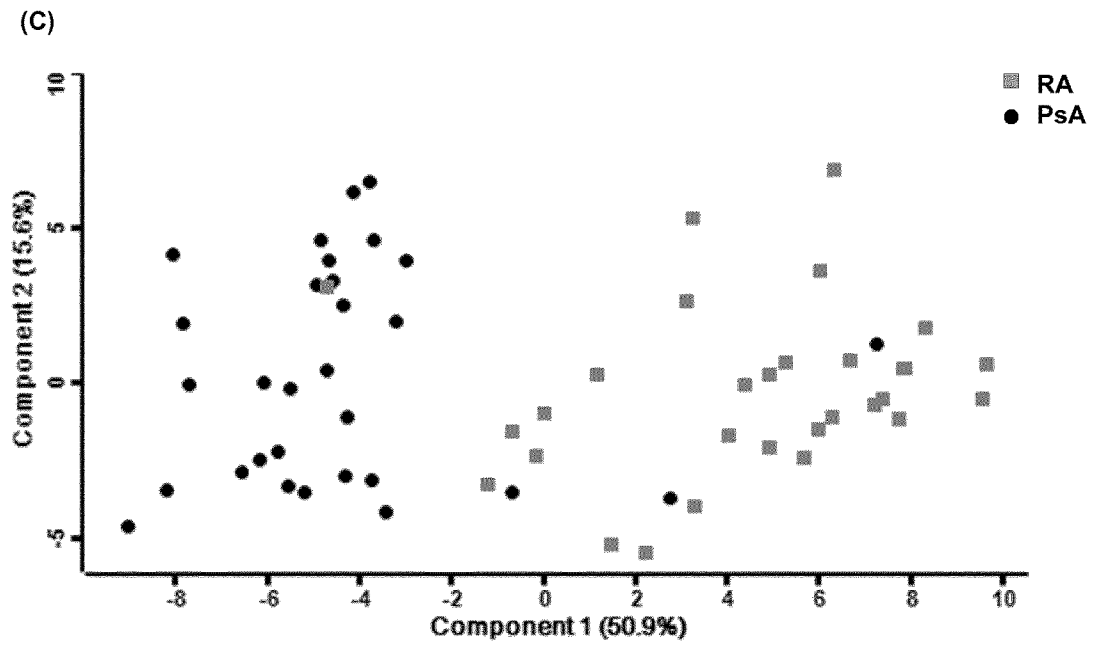

A total number of 64 patients were recruited, and a full description of the cohort is described in Szenpetery et al., "Striking difference of periarticular bone density change in early psoriatic arthritis and rheumatoid arthritis following anti-rheumatic treatment as measured by digital X-ray radio-grammetry". Rheumatology (Oxford), 2016. 55(5): p. 891-896. Recent-onset (symptom duration <12 months), treatment naïve PsA and RA patients with active joint inflammation, aged 18 to 80 years were enrolled consecutively. PsA patients (n=32) fulfilled the CASPAR criteria according to Taylor, W., et al., "Classification criteria for psoriatic arthritis: development of new criteria from a large international study". Arthritis Rheum, 2006. 54(8): p. 2665-73. and patients with RA (n=32) met the 2010 ACR/EULAR classification criteria for RA according to Aletaha, D., et al., "Rheumatoid arthritis classification criteria: an American College of Rheumatology/European League Against Rheumatism collaborative initiative". Arthritis Rheum, 2010. 62(9): p. 2569-81. Exclusion criteria were pregnancy, diseases of bone metabolism, previous treatment with disease-modifying anti-rheumatic drugs (DMARDs) or biologic agents, and treatment with anti-resorptive medications, para-thyroid hormone or strontium ranelate 6 months prior to the study. The use of calcium and vitamin D supplements and a stable dose of steroids of less than 10 mg/day were permitted during the study.

Label Free nLC-MS/MS Analysis

Prior to proteomic analysis, serum samples were depleted of 14 high abundant proteins (HAP) using the Agilent Multiple Affinity Removal System comprising a Hu-14 column (HuMARS14) (4.6×100 mm; Agilent Technologies, 5188-6557) on a Biocad Vision Workstation and subsequently trypsinized. Samples were run on a Thermo Q Exactive mass spectrometer according to the manufacturer's instructions.

Bioinformatic Data Analysis nLC-MS/MS data were visually inspected using Xcalibur software (2.2 SP1.48). MaxQuant (1.4.12) was then used for quantitative analysis of the Thermo Scientific .raw files while Perseus software (1.5.0.9) supported statistical analysis of the data.

SOMAscan Analysis

Individual patient serum samples were subjected to a multiplexed aptamer-based assay (SOMAscan) developed by Gold et al. to measure the levels of 1129 proteins as described by McArdle, A., et al., "Developing clinically relevant biomarkers in inflammatory arthritis: A multiplatform approach for serum candidate protein discovery". Proteomics Clin Appl, 2016. 10(6): p. 691-8.

Luminex Analysis

Individual serum samples were subjected to in-house developed and validated multiplexed immunoassays measuring 48 analytes using Luminex xMAP proteomics technology (Austin TX, USA). This analysis was undertaken by the Multiplex Core Facility Laboratory of Translational Immunology LTI, in the University Medical Centre Utrecht. The assays were performed as previously described by McArdle, A., et al. "Developing clinically relevant biomarkers in inflammatory arthritis: A multiplatform approach for serum candidate protein discovery". Proteomics Clin Appl, 2016. 10(6): p. 691-8.

RNAseq Analysis

Serum RNA was isolated using the miRNeasy serum/plasma kit (Qiagen) according to the manufacturer's instructions. RNA concentration was measured using the Nano-Drop Spectrophotometer. For each sample, 1.5 µL of RNA was reverse transcribed using the miScript reverse transcription kit (Qiagen) according to the manufacturer's instructions. Reverse transcription is based on a poly-A tailing of mature miRNAs followed by tailed oligo-dT reverse transcription. As such, all mature miRNAs in the RNA sample are reverse transcribed and amenable for qPCR detection. Individual cDNA samples were pooled, followed by a miRNA-specific pre-amplification and quantification using qPCR. In total, 2402 individual miRNAs were profiled using version 20 of the miRNome platform. Assays are spotted across 7×384-well plates. The qPCR mix contained a synthetic PCR template (PPC) that is used to assess PCR performance. The PPC assay was measured in duplicate for each sample on each miRNome assay plate. The number of detected miRNAs was determined by applying a Cq detection cut off of 29 cycles. miRNA analysis was carried out by Biogazelle, Gent, Belgium.

MRM Design and Optimisation

The development and optimisation of MRM assays was performed using Skyline software (version 3.6.0.1062) (MacCoss laboratory, Washington DC). Assays were developed to prototypic peptides for all proteins of interest according to the following criteria: no missed cleavages or 'ragged ends', sequence length between 4-25 amino acids. Where possible, peptides sequences with reactive (C) or methionine (M) residues were avoided but not excluded. A working MRM was determined based on the dot product ≥0.8, signal to noise ≥10, data points under the curve 10 and percentage coefficient of variance (retention time <1%, area ≤20%).

Sample Preparation for LC-MRM Analysis

Crude serum (2 µL) was added to the wells of a 96 deep-well plate (Thermo) and diluted 1 in 50 with $NH_4CO_3$. Rapigest™ SF surfactant/denaturant (Waters) was re-suspended in 50 mM $NH_4CO_3$ to give a stock solution of 0.1% w/v. The stock solution was added to each sample so that the final concentration of Rapigest™ was 0.05%. Plates were covered with adhesive foil and samples were incubated in the dark at 80° C. for 10 min. After incubation, plates were centrifuged at 2000rcf, 4° C. for 2 min to condense droplets. Following this, DTT was added to each sample at a final concentration of 20 mM. Samples were then incubated at 60° C. for 1 hr followed by centrifugation at 2000rcf, 4° C. for 2 min. Next, IAA was added to each sample to give a final concentration of 10 mM and plates were incubated at 37° C. in the dark for 30 min. Again, plates were centrifuged at 2000rcf at 4° C. for 2 min and samples were next diluted with LC-MS/MS grade $H_2O$ to give a final concertation of 25 mM $NH_4CO_3$. Trypsin was then added to each sample so that the protein enzyme ratio was 25:1. The reaction was stopped with the addition of 2 µL of neat TFA to each sample and incubation for a further 30 min at 37° C. In order to pellet Rapigest™, digests were transferred from 96-well plates to 1.5 mL to bind eppendorfs (Eppendorf) and centrifuged for 30 min at 12000rcf. Supernatants were removed and transferred into clean eppendorfs and lyophilised by speed vacuum at 30° C. for 2 hr. Lyophilised samples were stored at −80° C. until further use.

LC-MRM Analysis

MRM analysis was performed using an Agilent 6495 QqQ mass spectrometer with a JetStream electrospray source (Agilent) coupled to a 1290 Quaternary Pump HPLC system. Peptides were separated on an analytical on a Zorbax Eclipse plus C18, rapid resolution HT: 2.1×50 mm, 1.8 um, 600Bar column (Agilent) before introduction to the QqQ. A linear gradient of 3-75% over 17 mins was applied at a flow rate of 0.400 μL/min with a column oven temperature of 50° C. Source parameters were as follows, gas temp: 150° C., gas flow 15 L/min, nebuliser psi30, sheath gas temp 200° C. sheath gas flow 11 L/min. Peptide retention times and optimised collision energies were supplied to MassHunter (B0.08 Agilent Technologies) to establish a dynamic MRM scheduling method based on input parameters of 800 ms cycle times and 2 min retention time windows. Percentage coefficient of variance (% Cv) of biological and technical replicates was used as a measure of variance and was calculated using the standard calculation of % Cv=(standard deviation/mean)*100.

Enzyme Linked Immunosorbent Assay Analysis

CRP levels were evaluated using the "gold" standard clinical grade assay in St Vincent's University Hospital, Dublin. 125 μL of serum from each patient was analysed for levels of CRP using an automated CRPL3 Tina-quant C-Reactive Protein assay (Roche Diagnostics, GmbH).

Statistical Analysis

Graph pad Prism software package (7.00) were used to investigate the statistical significance of Luminex and miRNA data whereas SOMAsuite (1.0) was used to analyse SOMAscan data. The ability of quantified proteins/peptides and miRNAs to predict the diagnosis (PsA or RA) of individual patients was assessed using the random Forest package in R (version 3.3.2). The most important variables in providing the area under the receiver operating curve were selected by use of the variable importance index and the Gini decrease in impurity was used to assess the importance of each variable. All AUC values were determined using the ROCR package in R (version 3.3.2).

Example 1

Patient Sample Characterisation and Study Design

Serum samples were collected from 32 PsA and 32 RA patients. The demographic and clinical features of patients are summarised in Table 1.

TABLE 1

| | Baseline demographics and clinical parameters of 64 patients with early inflammatory arthritis. | | |
|---|---|---|---|
| | Total (n = 64) | PsA (n = 32) | RA (n = 32) |
| Age (years) | 43.58 ± 13.25 | 39.56 ± 11.14 | 47.59 ± 14.13 |
| Female/Male n(%) | 37(58)/27(42) | 15(47)/17(53) | 22(69)/10(31) |
| aCCP [+] n(%) (normal 0-6.9) | 33 (52) | 7 (22) | 26 (81) |
| RF [+] n(%) (normal 0-25) | 25 (39) | 0 | 25 (78) |
| ESR (mm/h) | 19.4 ± 16.8 | 12 ± 8.1 | 26.7 ± 20 |
| CRP (mg/L) (normal <5) | 14.4 ± 19.8 | 6.6 ± 8.3 | 22.2 ± 24.6 |
| DAS28-CRP | 4.2 (1.66-6.88) | 3.7 (2.1-5.8) | 4.9 (1.7-6.9) |
| TJC (0-28 joints) | 6 (0-23) | 4 (0-20) | 8.5 (0-23) |
| SJC (0-28 joints) | 2 (0-12) | 1 (0-5) | 3.5 (0-12) |
| Dactylitis n(%) | | 10 (31) | |
| BMI (kg/cm²) | 28.1 ± 6.27 | 27.97 ± 6.32 | 28.24 ± 6.32 |
| PASI | | 3.35 (0-27.7) | |

Unbiased nLC-MS/MS Based Protein Analysis

To investigate differences in serum protein expression between patients, individual depleted samples were analysed by nLC-MS/MS on a QExactive mass spectrometer. A total of 451 proteins were identified across all samples analysed.

To identify proteins that were differentially expressed between patients with PsA from those with RA (a) univariate analysis was applied to 121 commonly identified proteins in these patient samples and (b) multivariate analysis was applied to the complete data set. Univariate analysis (student T test using a Benjamini Hochberg FDR 0.01) revealed that 66 proteins were significantly differentially expressed between PsA and RA patients.

Hierarchical cluster and principle component analysis was carried out on these 66 proteins and this demonstrated in an unbiased manner, the overall differences/similarities between expression levels in the individual PsA and RA patients. Clear within group clustering and between group separations could be observed (see FIG. 1).

Random forest analysis on the 451 proteins revealed patients could be segregated with an AUC of 0.94 (see Table 3; ROC plot of FIG. 3A). Thus, this data clearly reflected a difference in the serum protein profile between PsA and RA patients.

TABLE 3

Pattern of expression changes in peptides measured by MRM and LC-MS/MS.
Peptides were analysed in PsA (n = 30) and RA (n = 30) patient samples
during LC-MS/MS analysis of depleted serum) and MRM analysis of crude serum.

| # | Accession | UniProt ID | Gene Name | Protein | Peptide | Pattern of Expression MRM Vs LC-MS/MS | |
|---|---|---|---|---|---|---|---|
| | | | | | | Concordance | Discordance |
| 1 | A0N5G1 | A0N5G1 | V-kappa-1 | Rheumatoid factor C6 light chain | ASSLESGVPSR | ↑RA | |
| 2 | P02763 | A1AG | ORM1 | Alpha 1 acid glycoprotein | SDWYTDWK | ↑RA | |
| 3 | P01009 | A1AT | SERPINA1 | Alpha 1 antitrypsin | SVLGQLGITK | ↑RA | |
| 4 | P01009 | A1AT | SERPINA1 | Alpha 1 antitrypsin | LSITGTYDLK | ↑RA | |
| 5 | P02750 | A2GL | LRG1 | Leucine rich alpha 2 glycoprotein | VAAGAFQGLR | | x |
| 6 | P01011 | ACT | AACT | alpha-1-antichymotrypsin | ADLSGITGAR | ↑RA | |
| 7 | P35858 | ALS | IFGALS | Insulin-like growth factor binding complex acid labile subunit | LEYLLLSR | | x |
| 8 | Q8J001 | AT3 | AT3 | Antithrombin | SLNPNR | NA | NA |
| 9 | P04003 | C4BPA | C4BPA | C4b-binding protein alpha chain | LSLEIEQLELQR | | x |
| 10 | P00450 | CERU | CP | Ceuroplasmin | ALYLQYTDETR | ↑RA | |
| 11 | P00450 | CERU | CP | Ceuroplasmin | GAYPLSIEIGVR | ↑RA | |
| 12 | P00751 | CFAB | CFB | Complement factor B | VSEADSSNADWVTK | | x |
| 13 | P10909 | CLUS | CLU | Clusterin | TLLSNLEEAK | | x |
| 14 | P0C0L5 | CO4B | C4B | Complement C4-B | GSSTWLTAFVLK | ↑PsA | |
| 15 | P02775 | CXCL7 | PPBP | Platelet basic protein | NIQSLEVIGK | ↑PsA | |
| 16 | Q16610 | ECM1 | ECM1 | Extracellular matrix protein | AWEDTLDK | ↑PsA | x |
| 17 | P03951 | FA11 | F11 | Coagulation factor X | DIYVDLDMK | ↑PsA | |
| 18 | P00738 | HPT | HP | Haptoglobin | VTSIQDWVQK | ↑RA | |
| 19 | P00739 | HPTR | HPR | Haptoglobin-related protein | GSFPWQAK | ↑RA | |
| 20 | Q14624 | ITH4 | ITH4 | Inter-alpha-trypsin inhibitor heavy chain | SIQNNVR | ↑RA | |
| 21 | P01042 | KNG1 | KNG1 | Kininogen | YFIDFVAR | | x |

TABLE 3-continued

Pattern of expression changes in peptides measured by MRM and LC-MS/MS.
Peptides were analysed in PsA (n = 30) and RA (n = 30) patient samples
during LC-MS/MS analysis of depleted serum) and MRM analysis of crude serum.

| # | Accession | UniProt ID | Gene Name | Protein | Peptide | Pattern of Expression MRM Vs LC-MS/MS Concordance | Pattern of Expression MRM Vs LC-MS/MS Discordance |
|---|---|---|---|---|---|---|---|
| 22 | P18428 | LBP | LBP | Lipopolysaccharide-binding protein | ITLPDFTGDLR | ↑RA | |
| 23 | P36955 | PEDF | SERPINF1 | Pigment epithelium-derived factor | SSFVAPLEK | ↑PsA | |
| 24 | P04070 | PROC | PROC | Vitamin K-dependent protein C | TFVLNFIK | NA | NA |
| 25 | P04070 | PROC | PROC | Vitamin K-dependent protein C | SGWEGR | NA | NA |
| 26 | P00734 | THRB | F2 | Prothombin | ETWTANVGK | ↑PsA | |
| 27 | P07996 | TSP1 | THBS1 | Thrombospondin | FVFGTTPEDILR | ↑RA | |

TABLE 4A

| # | Accession | UniProt ID | Protein | Peptide | SEQ ID NO: |
|---|---|---|---|---|---|
| 1 | A0N5G1 | A0N5G1 | Rheumatoid factor C6 light chain | ASSLESGVPSR | 1 |
| 2 | P02750 | A2GL | Leucine-rich alpha-2-glycoprotein | VAAGAFQGLR | 2 |
| 3 | P02750 | A2GL | Leucine-rich alpha-2-glycoprotein | ADLSGITGAR | 3 |
| 4 | P02750 | A2GL | Leucine-rich alpha-2-glycoprotein | TLDLGENQLETLPPDLLR | 4 |
| 5 | P01011 | AACT | Alpha-1-antichymotrypsin His-Pro-less | ADLSGITGAR | 5 |
| 6 | P01011 | AACT | Alpha-1-antichymotrypsin His-Pro-less | EIGELYLPK | 6 |
| 7 | P01011 | AACT | Alpha-1-antichymotrypsin His-Pro-less | ITLLSALVETR | 7 |
| 8 | P0C0L5 | CO4B | Complement C4-B | GSSTWLTAFVLK | 8 |
| 9 | P0C0L5 | CO4B | Complement C4-B | GLEEELQFSLGSK | 9 |
| 10 | P03951 | FA11 | Coagulation factor XI | DIYVDLDMK | 10 |
| 11 | P03951 | FA11 | Coagulation factor XIa light chain | DSVTETLPR | 11 |
| 12 | P00738 | HPT | Haptoglobin | VTSIQDWVQK | 12 |
| 13 | P00738 | HPT | Haptoglobin | VGYVSGWGR | 13 |
| 14 | P00738 | HBB1 | Hemoglobin subunit gamma | LLVVYPWTQR | 14 |
| 15 | P00738 | HBB1 | Hemoglobin subunit beta | VNVDEVGGEALGR | 15 |
| 16 | P00738 | HPT | Haptoglobin | VGYVSGWGR | 16 |
| 17 | P00739 | HPTR | Haptoglobin-related protein | GSFPWQAK | 17 |
| 18 | P07996 | TSP1 | Thrombospondin-1 | FVFGTTPEDILR | 18 |

TABLE 4B

| # | Accession | UniProt ID | Protein | Peptide | SEQ ID NO: |
|---|---|---|---|---|---|
| 1 | P02763 | A1AG | Alpha-1-acid glycoprotein 1 | SDVVYTDWK | 19 |
| 2 | P01009 | A1AT | Alpha-1-antitrypsin | SVLGQLGITK | 20 |
| 3 | P01009 | A1AT | Alpha-1-antitrypsin | SITGTYDLK | 21 |
| 4 | P35858 | ALS | Insulin-like growth factor-binding protein complex acid labile subunit | LEYLLLSR | 22 |
| 5 | Q8J001 | Q8J001 | Antithrombin | SLNPNR | 23 |
| 6 | P04003 | C4BPA | C4b-binding protein alpha chain | LSLEIEQLELQR | 24 |
| 7 | P04050 | CERU | Ceruloplasmin | ALYLQYTDETFR | 25 |
| 8 | P04005 | CERU | Ceruloplasmin | GAYPLSIEPIGVR | 26 |
| 9 | P00751 | CFAB | Complement factor B | VSEADSSNADWVTK | 27 |
| 10 | P10909 | CLUS | Clusterin | VSEADSSNADWVTK | 28 |
| 11 | P02775 | CXCL7 | Platelet basic protein | NIQSLEVIGK | 29 |

TABLE 4B-continued

| # | Accession | UniProt ID | Protein | Peptide | SEQ ID NO: |
|---|---|---|---|---|---|
| 12 | Q16610 | ECM1 | Extracellular matrix protein 1 | AWEDTLDK | 30 |
| 13 | Q14624 | ITH4 | Inter-alpha-trypsin inhibitor heavy chain H4 | SIQNNVR | 31 |
| 14 | P01042 | KNG1 | Kininogen-1 | YFIDFVAR | 32 |
| 15 | P18428 | LBP | Lipopolysaccharide-binding protein | ITLPDFTGDLR | 33 |
| 16 | P36955 | PEDF | Pigment epithelium-derived factor | SSFVAPLEK | 34 |
| 17 | P04070 | PROC | Vitamin K-dependent protein C | TFVLNFIK | 35 |
| 18 | P04070 | PROC | Vitamin K-dependent protein C | SGWEGR | 36 |
| 19 | P00743 | THRB | Prothrombin | ETWTANVGK | 37 |

TABLE 4C

| # | Accession | UniProt ID | Protein | Peptide | SEQ ID NO: |
|---|---|---|---|---|---|
| 1 | P06396 | GELS | Gelsolin | EVQGFESATFLGYFK | 38 |
| 2 | Q14315 | FLNC | Filamin-C | NDNDTFTVK | 39 |
| 3 | P02748 | CO9 | Complement component C9b | TSNFNAAISLK | 40 |
| 4 | P32119 | PRDX2 | Peroxiredoxin-2 | TDEGIAYR | 41 |
| 5 | P05155 | IPSP | Plasma serine protease inhibitor | QLELYLPK | 42 |
| 6 | P05154 | IPSP | Adenosine deaminase 2 | IGHGFALSK | 43 |
| 7 | P02748 | CO9 | Complement component C9b | LSPIYNLVPVK | 44 |
| 8 | P20742 | PZP | Pregnancy zone protein | SSGSLLNNAIK | 45 |
| 9 | Q5VU43 | PDE4DIP | Myomegalin | IYFLEER | 46 |
| 10 | P05090 | APOD | Apolipoprotein D | VLNQELR | 47 |
| 11 | P07359 | GP1BA | Glycocalicin | LTSLPLGALR | 48 |
| 12 | P43652 | AFM | Afamin | FLVNLVK | 49 |
| 13 | P05155 | IC1 | Plasma protease C1 inhibitor | LLDSLPSDTR | 50 |
| 14 | Q06033 | ITIH3 | Inter-alpha-trypsin inhibitor heavy chain H3 | ALDLSLK | 51 |
| 15 | Q06033 | ALS | Insulin-like growth factor-binding protein 3 | FLNVLSPR | 52 |
| 16 | Q08380 | LG3BP | Galectin-3-binding protein | SDLAVPSELALLK | 53 |
| 17 | P02765 | FETUA | Alpha-2-HS-glycoprotein chain B | AHYDLR | 54 |
| 18 | P01008 | AT3 | Antithrombin-III | VGDTLNLNLR | 55 |

Example 2

SOMAscan and Luminex Targeted Protein Analysis

To extend the breadth of proteome coverage afforded by nLC-MS/MS, samples were also analysed on 2 alternative and complementary protein biomarker discovery platforms. SOMAscan analysis supported the quantification of 1129 proteins in a subset of patient samples PsA (n=18) and RA (n=18). Univariate analysis of these data revealed that 175 proteins were significantly differentially expressed between PsA and RA patients (see Table 2).

TABLE 2

Determination of protein signatures to predict diagnosis in patients with early PsA and RA. Area under the curve (AUC) values were generated using the predicted probabilities from the random forest model used to discriminate between the groups.

| Platform | n | Correctly predicted | AUC |
|---|---|---|---|
| LC-MS/MS | 60 | 55/60 | 0.94 |
| Luminex | 64 | 43/64 | 0.69 |

TABLE 2-continued

Determination of protein signatures to predict diagnosis in patients
with early PsA and RA. Area under the curve (AUC) values were
generated using the predicted probabilities from the random
forest model used to discriminate between the groups.

| Platform | n | Correctly predicted | AUC |
|---|---|---|---|
| SOMAscan | 36 | 26/36 | 0.75 |
| miRNA | 63 | 36/63 | 0.55 |
| Combined Omic | 36 | 31/36 | 0.90 |

Multivariate analysis revealed that it was possible to discriminate PsA from RA patients with an AUC of 0.73 (Table 3; ROC plot of FIG. 3B).

Figure 4:
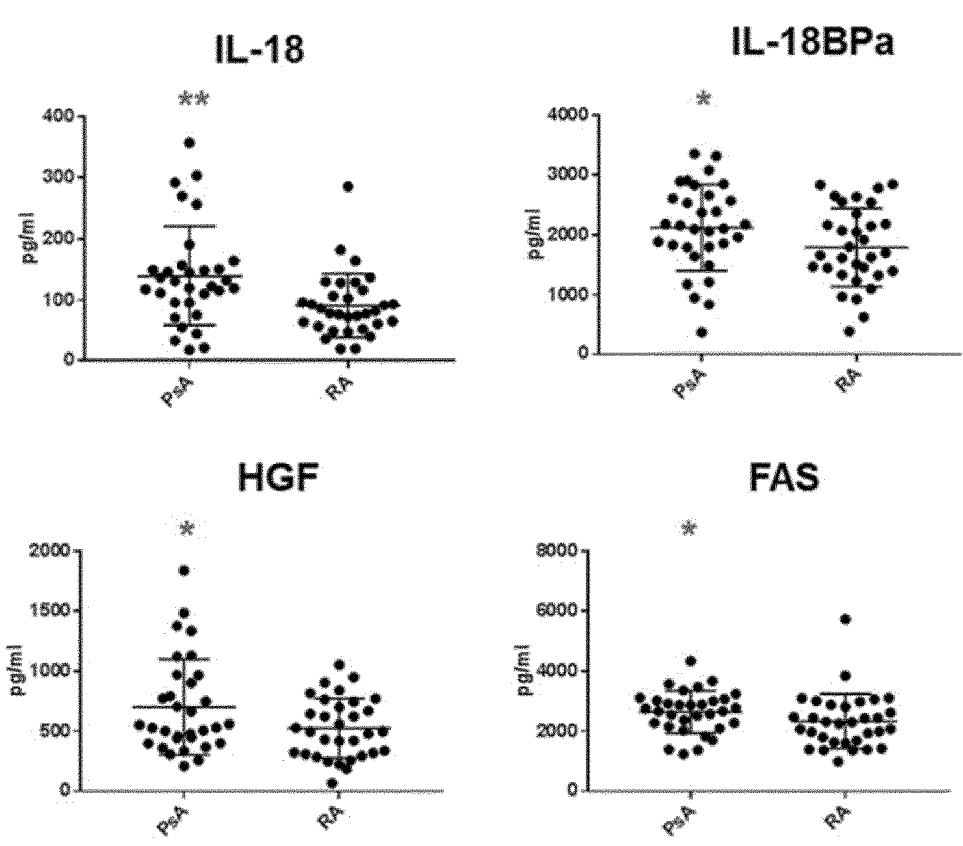
FIG. 4 illustrates serum proteins measured by Luminex analysis were significantly differently expressed between PsA and RA patients, wherein Luminex analysis of serum samples revealed (A) IL-18 ($p \leq 0.001$) II-18 BPa, HGF and FAS ($p \leq 0.05$) were differentially expressed between PsA (n=32) and RA(n=32)

Based on their known importance in PsA and RA, 48 proteins were selected for analysis using the Luminex assay. Of the 48 proteins targeted, 23 were identified in every sample. T-tests revealed that 4 proteins; IL-18 ($p \leq 0.001$) Il-18 BPa, HGF, and FAS ($p \leq 0.05$) were significantly differentially expressed between PsA and RA samples (see FIG. 4).

Figure 3:
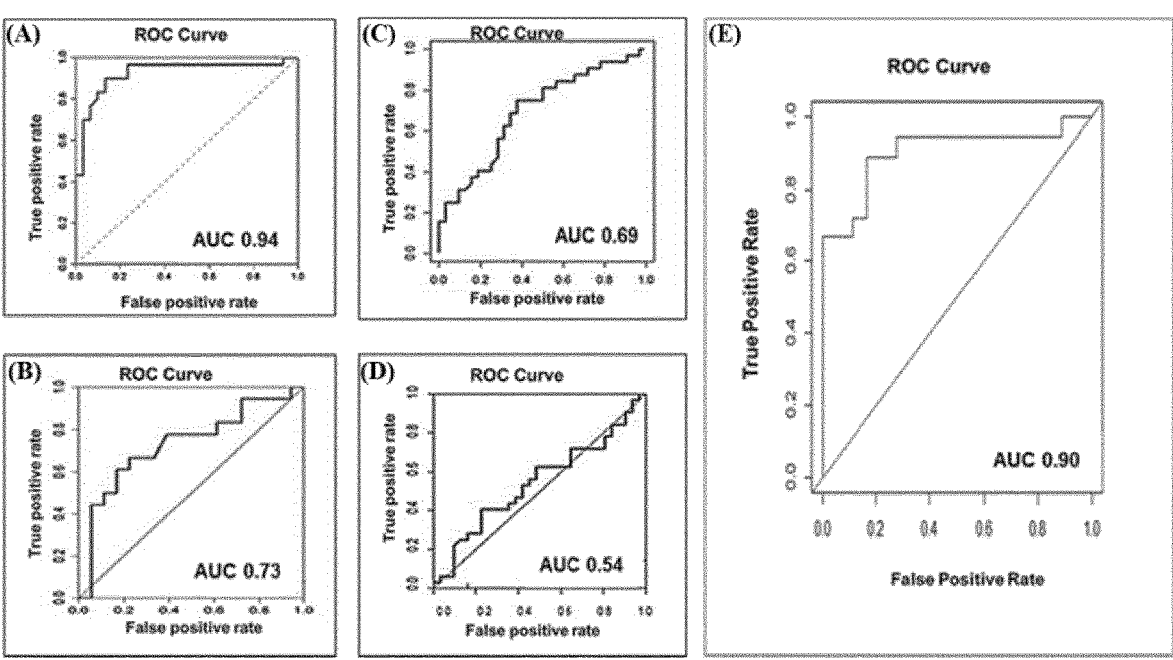
FIG. 3 illustrates ROC analysis of (A) LC-MS/MS (n=60), (B) SOMAscan (n=36), (C) Luminex (n=64), (D) RNA seq (n=63), and (E) Combined matched (n=36) data.

Random forest analysis of the Luminex data demonstrated patients could be segregated with an AUC of 0.64 (see Table 3; FIG. 3C). In comparison to the LC-MS/MS analysis, the targeted approach to protein discovery yielded data sets with reduced predictive power.

Example 3

RNAseq Based miRNA Analysis

Figure 5:
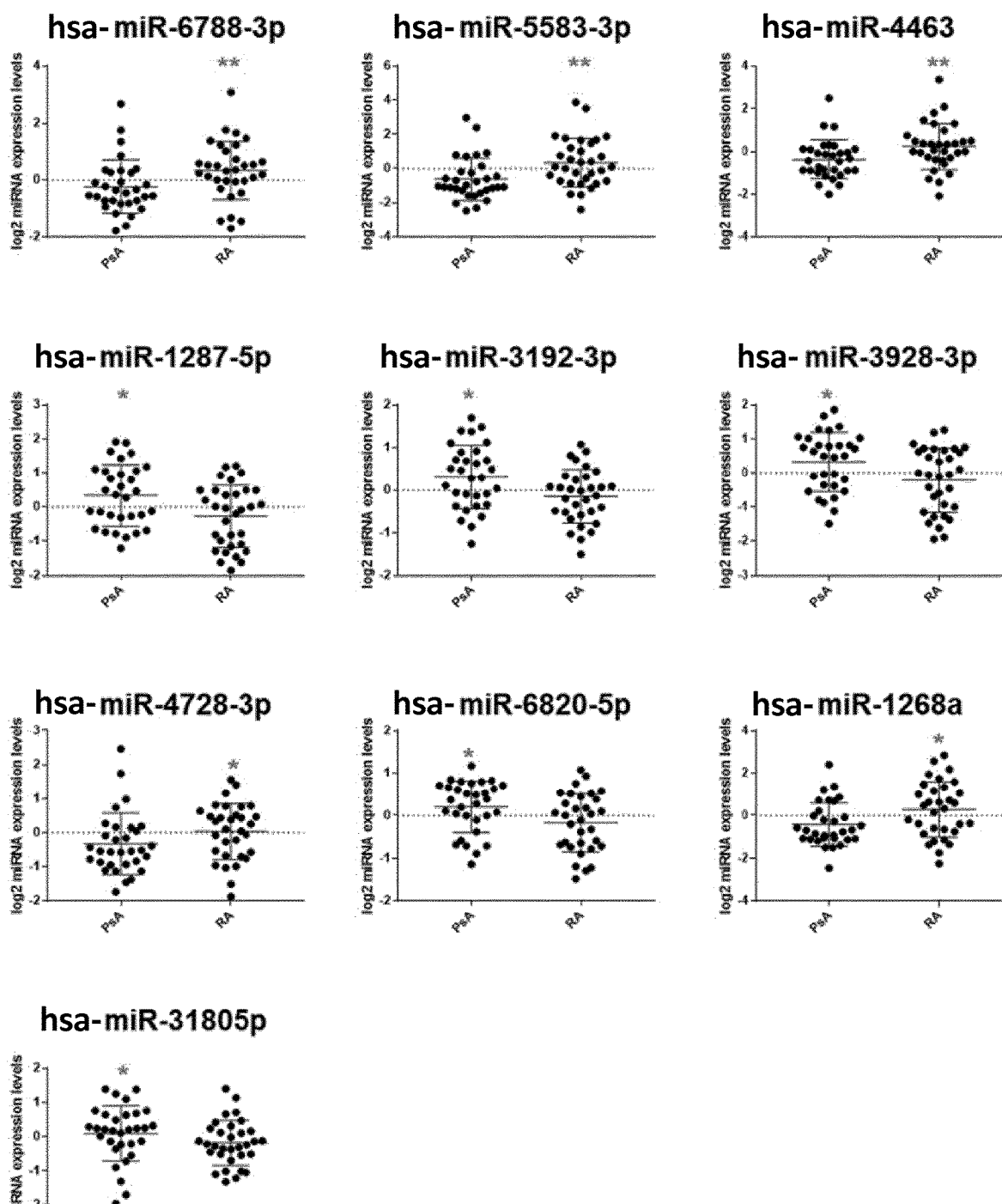
FIG. 5 illustrates serum miRNAs measured in PsA and RA patients, wherein 10 miRNAs were significantly differentially expressed PsA Vs RA and RA GR Vs NR patients respectively ($p \leq 0.05$).

The miRNAome of baseline PsA (n=31) and RA (n=32) samples were analysed using a miRNA array. A total of 376 miRNAs were identified of which 178 were commonly expressed in each sample. Using a Mann Whitney U-test it was found that of the 178 common miRNAs analysed 10 were significantly differentially expressed between PsA and RA (see Table 3; FIG. 5).

Random forest analysis of the 376 miRNA data set revealed it was possible to correctly classify only 36/63 patients resulting an AUC of 0.55 (see ROC plot of FIG. 3D). This data indicated that the serum miRNA profile between PsA and RA patients was not different.

Example 4

Multivariate Analysis of Combined Omic Data

In an attempt to directly compare platforms, the combined matched data set (i.e. from the same 36 samples analysed on each platform) were analysed. Results showed that it was possible to distinguish PsA from RA patients with an AUC of 0.90 (see Table 3; ROC plot of FIG. 3E). The weighted variable importance, which was assessed by a mean decrease in Gini, demonstrated that, out of the top 30 analytes contributing to this AUC, 28 were proteins (19 of which were identified by nLC-MS/MS and 9 by SOMAscan) and 2 were miRNAs. These same proteins and miRNAs were observed as statistically significant during uni- and/or multivariate analysis of the individual protein and miRNA datasets. Taken together, the LC-MS/MS data emerged as the most promising and the proteins identified by nLC-MS/MS were prioritised for further evaluation as the most time- and cost-effective strategy.

Example 5

LC-MRM Evaluation of nLC-MS/MS Identified Biomarkers

Figure 2:
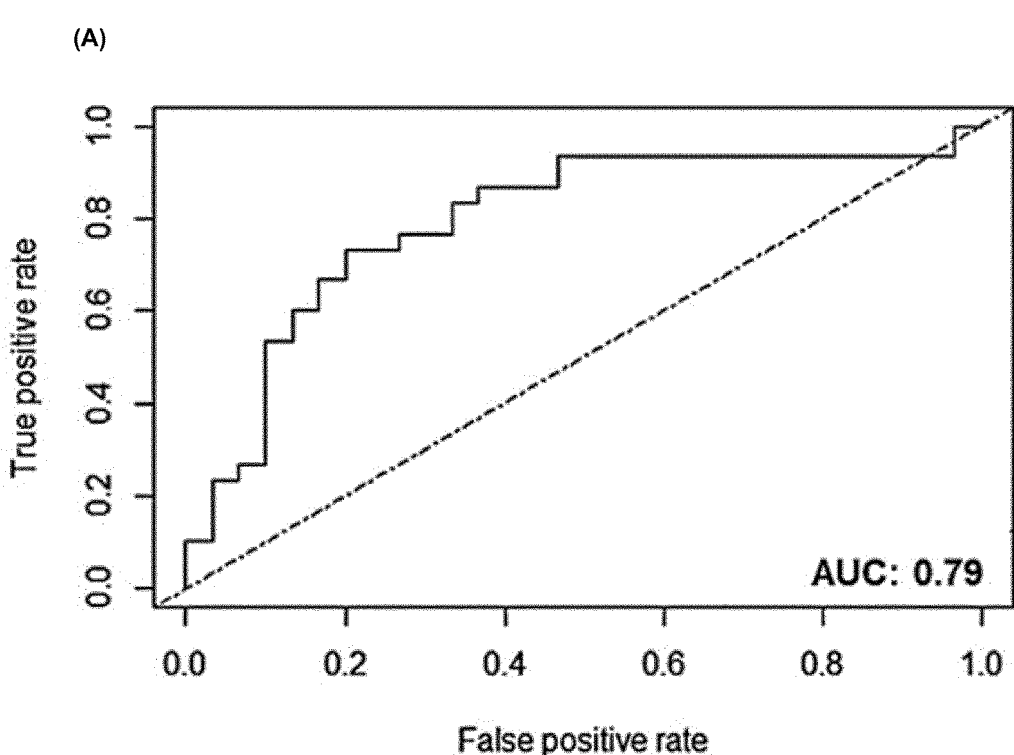
FIG. 2 illustrates the association between protein expression and differential diagnosis (A) ROC analysis of LC-MRM data (n=60), (B) MRM and MS/MS spectrum for CRP, (C) Levels of CRP analysed by ELISA ($p \leq 0.009$) and MRM ($p \leq 0.006$) (D) Pearson correlation between ELISA and CRP measurements ($R^2$ 0.8345)
Figure 2:
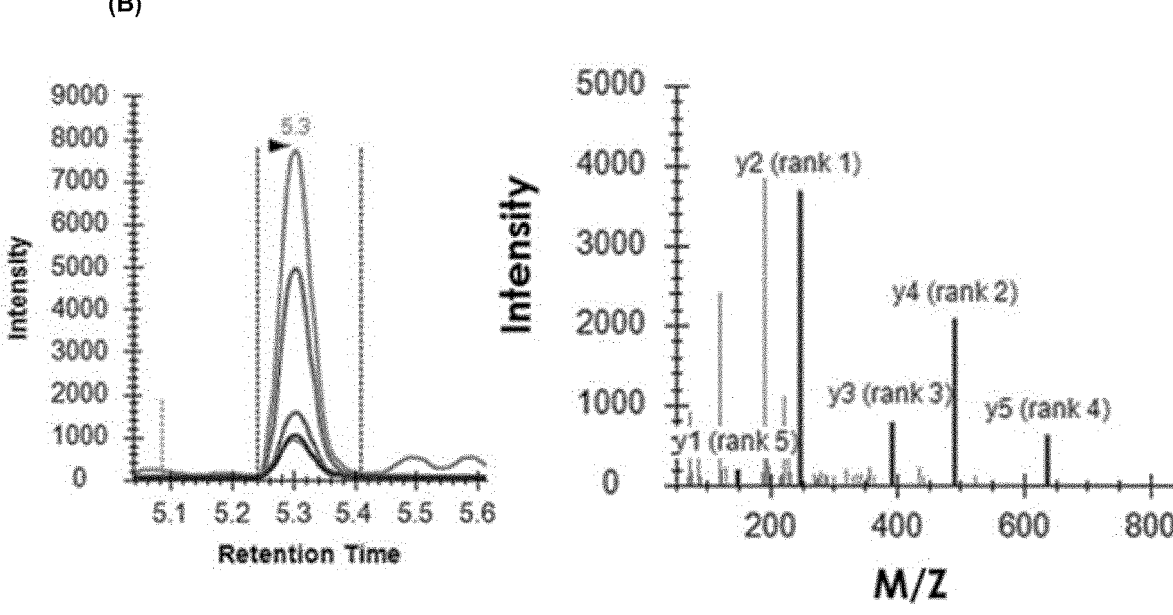
Figure 2:
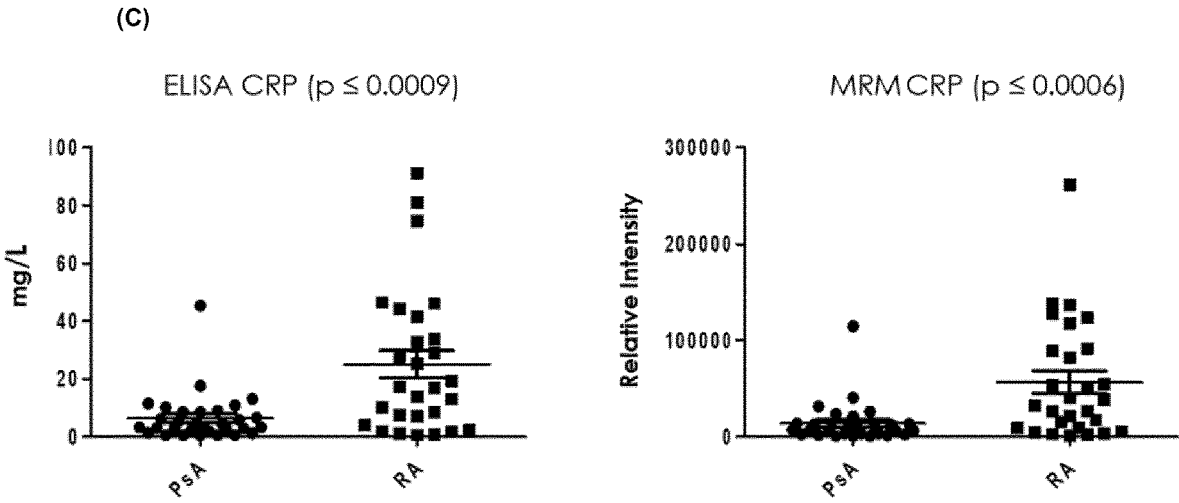

A total of 233 proteins represented by 735 peptides and 3735 transitions (5 per peptide) were brought forward for MRM assay development. These candidates included proteins identified by uni-/multi-variate analysis of the discovery data described here in addition to proteins identified during previous studies in pooled patient samples. Of the proteins brought forward, it was possible to develop an assay for 150 of them represented by 299 peptides. These peptides were measured in the 64 clinical samples in a randomised run order. Random forest analysis of the data revealed it was possible to discriminate between PsA and RA patients with an AUC of 0.79 (see Table 3; FIG. 2A).

The top 27 most important peptides in providing this AUC were selected by use of the variable importance index, here the Gini decrease in impurity was used to assess the importance of each variable.

Peptide expression changes observed during LC-MRM analysis were next compared to those observed during nLC-MS/MS analysis. Comparisons could be made for 24/27 peptides since for 3 peptides nLC-MS/MS data was not available. Thus, it was found that for 17/24 peptides, expression changes in PsA and RA patients were in agreement when analysed by both MRM and nLC-MS/MS (5 upregulated in PsA and 12 upregulated in RA) supporting their genuine value as putative biomarkers. For the remaining 7/24 peptides, a potential reason for discordance in observations may be due to false discoveries introduced during the initial LC-MS/MS analysis whereby workflows employed were less robust compared to those used during MRM analysis (Table 3). Finally, a MRM assay was developed to CRP (see FIG. 2B) with analysis of this protein by standard lab assay serving as a comparator. It was not surprising to find that serum levels of CRP were significantly upregulated in patients with RA (n=30) as compared to those PsA (n=30) when measured by both ELISA ($p \leq 0.0009$) and MRM ($p \leq 0.0006$) (see FIG. 2C) and these measurements could be correlated ($R^2 = 0.8345$) (see FIG. 2D).

The present invention identifies biomarkers for the differentiation of patients with PsA from those with RA. Importantly, the invention is based on multiplexed analysis of serological markers in patients with early onset PsA. Here it was established that patients with PsA could be differentiated from those with RA based on molecular signatures identified in serum. Multi-omic analysis revealed it was possible to discriminate PsA from RA patients with an AUC of 0.94 (nLC-MS/MS), AUC 0.69 (Luminex), AUC 0.73 (SOMAscan) and AUC 0.55 (miRNA), while combining data from a group of matched patients resulted in an AUC of 0.90.

Example 6

Independent Evaluation of Candidate Serum Protein Biomarkers for Differentiation of Psoriatic from Rheumatoid Arthritis To further identify serological protein biomarkers for the stratification of patients with psoriatic arthritis (PsA) from those with rheumatoid arthritis (RA) at early stages of the disease, the serum proteome of patients with PsA and RA was interrogated using liquid chromatography mass spectrometry (LC-MS/MS). Multiple reaction monitoring (MRM) assays were developed to 206 proteins and subsequently analysed using a triple quadrupole mass spectrometer.

Recent-onset (symptom duration <12 months), treatment-naïve PsA and RA patients with active joint inflammation, aged 18 to 80 years, were enrolled consecutively. PsA patients (n=94) fulfilled the CASPAR criteria and patients with RA (n=72) met the 2010 ACR/EULAR classification criteria for RA. Exclusion criteria were pregnancy, diseases of bone metabolism, previous treatment with disease-modifying anti-rheumatic drugs (DMARDs) or biologic agents, and treatment with anti-resorptive medications, parathyroid hormone or strontium ranelate 6 months prior to the study. The use of calcium and vitamin D supplements and a stable dose of steroids of less than 10 mg/day were permitted during the study.

The development and optimisation of MRM assays was performed using Skyline software (MacCoss laboratory, Washington DC). Assays were developed to proteotypic peptides for all proteins of interest according to the following criteria: no missed cleavages or 'ragged ends', sequence length between 4-25 amino acids. Where possible, peptides sequences with reactive (C) or methionine (M) residues were avoided but not excluded. A working MRM was determined based on the dot product ≥0.8, signal to noise ≥10, data points under the curve 10 and percentage coefficient of variance (retention time ≤1%, area ≤20%).

Serum samples were collected from 94 PsA and 72 RA patients. The demographic and clinical features of patients are summarised in Table 4.

TABLE 4

Demographic and clinical features of patients:

Discovery and verification:

|  | PsA (n = 32) | RA (n = 32) |
|---|---|---|
| Age (years) | 39.56 ± 11.14 | 47.59 ± 14.13 |
| Female/Male n(%) | 15(47)/17(53) | 22(69)/10(31) |
| aCCP [+] n(%) (normal 0-6.9) | 7 (22) | 26 (81) |
| CRP (mg/L) (normal <5) | 6.6 ± 8.3 | 22.2 ± 24.6 |
| Dactylitis n(%) | 10 (31) | — |
| PASI | 3.35 (0-27.7) | — |

Validation:

|  | PsA (n = 95) | RA (n = 72) |
|---|---|---|
| Age | 52.52 +/− 6.59 | 55.08 +/− 9.62 |
| Female/Male (%) | 51(54)/44(46) | 38(53)/34(47) |
| aCCP [+] n(%) | 1 (1) | 49 (74) |
| CRP | 4.74 +/− 6.66 | 20.96 +/− 34.16 |
| Dactylitis | 46 (52) | — |
| PASI | 2.69 (0-14) | — |

* n = 90
n = 66
** n = 86
n = 71

Crude serum (2 μl) was added to the wells of 96-deep-well plates and digested with trypsin. Tryptic digestion was performed in a flat-bottom polystyrene 96-well plate following an in-house developed standard operating procedure (SOP18A). For protein denaturation, 25 μL denaturant solution (50% trifluoroethanol (TFE) in 50 mM NH₄HCO₃ with 10 mM dithiothreitol (DTT)) were added to 2 μL serum in each well. The 96-well plate was covered with a sterile adhesive foil and incubated for 45 min at 60° C. To remove any condensation from the foil, samples were allowed to cool down to room temperature and centrifuged for 2 min at 4000 g. 10 μL of 120 mM iodoacetamide (IAA) solution was added to each sample, the plate was sealed, vortexed and incubated for 30 min protected from light. To quench the excess of IAA, 10 μL of 50 mM DTT was added to each well. The plate was then re-sealed, vortexed and incubated for 30 min protected from light before diluting samples by adding 190 μL of 12.5 mM NH₄HCO₃ solution. For each well 5.5 μL trypsin solution (0.2 mg/mL sequencing grade modified trypsin (Promega) re-suspended 1:1 in trypsin resuspension buffer (Promega) and 50 mM NH₄HCO₃) was used. After 18h incubation at 37° C., 5 μL of 25% formic acid (FA) was added to each well in the 96-well plate. The digestion plates were stored at −80° C. once the digestion process was complete.

A total of 206 proteins represented by 423 peptides were used for the MRM assay, which was applied to 166 patient samples. MRM analysis was performed using an Agilent 6495 triple quadrupole (QqQ) mass spectrometer with a JetStream electrospray source (Agilent) coupled to a 1290 Quaternary Pump HPLC system. Peptides were separated on an analytical Zorbax Eclipse plus C18, rapid resolution HT: 2.1×50 mm, 1.8 um, 600 Bar column (Agilent) before introduction to the QqQ. A linear gradient of 3-75% over 17 mins was applied at a flow rate of 0.400 μl/min with a column oven temperature of 50° C. Source parameters were as follows, gas temp: 150° C., gas flow 15 l/min, nebuliser psi 30, sheath gas temp 200° C. and sheath gas flow 11 l/min. Peptide retention times and optimised collision energies were supplied to MassHunter (B0.08 Agilent Technologies) to establish a dynamic MRM scheduled method based on input parameters of 800 millisecond (ms) cycle times and 2 min retention time windows. The percentage coefficient of variance (% Cv) of biological and technical replicates was used as a measure of variance and was calculated using the standard calculation of % Cv=(standard deviation/mean) 100.

The ability of quantified proteins/peptides to predict the diagnosis (PsA or RA) of individual patients was assessed using the random Forest package in R (version 3.3.2). The most important variables in providing the area under the receiver operating curve were selected by use of the variable importance index and the Gini decrease in impurity was used to assess the importance of each variable. All area under the curve (AUC) values were determined using the ROCR package in R (version 3.3.2).

Multivariate analysis of the data revealed it was possible to discriminate PsA from RA patients with an area under the curve (AUC) of between 0.844 and 0.901. The most important peptides in providing this AUC were selected by use of the variable importance index—the Gini decrease in impurity was used to assess the importance of each variable.

The invention claimed is:

1. A method of treating psoriatic arthritis in a subject, the method comprising:
   (a) determining the quantitative or qualitative level of two or more peptides in a blood sample from a subject, the two or more peptides comprising a peptide of Rheumatoid factor C6 light chain having an amino acid sequence ASSLESGVPSR (SEQ ID NO:1) and a peptide of Leucine-rich alpha-2-glycoprotein having an amino acid sequence VAAGAFQGLR (SEQ ID NO: 2); and
   (b) differentiating psoriatic arthritis from rheumatoid arthritis in the subject, wherein the quantitative or qualitative level of Rheumatoid factor C6 light chain is increased in rheumatoid arthritis, and treating the subject with a therapy for psoriatic arthritis selected from the group consisting of methotrexate, an anti-TNFα inhibitor, ustekinumab, apremilast, and an anti-IHL17 therapy.

2. A method according to claim 1, further comprising determining the quantitative or qualitative level of one or more further biomarkers selected from: Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

3. A method according to claim 1, further comprising determining the quantitative or qualitative level of one or more further biomarkers selected from: Gelsolin; Filamin-C;

Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

4. A method of treating psoriatic arthritis in a subject, the method comprising:
   (a) determining the quantitative or qualitative level in a blood sample from a subject of Rheumatoid factor C6 light chain peptide having an amino acid sequence of SEQ ID NO:1 and Leucine-rich alpha-2-glycoprotein peptide having an amino acid sequence of SEQ ID NO:2, wherein the level is measured by performing mass spectrometry comprising multiple reaction monitoring (MRM); and
   (b) differentiating psoriatic arthritis from rheumatoid arthritis in the subject, wherein the quantitative or qualitative level of Rheumatoid factor C6 light chain is increased in rheumatoid arthritis, and treating the subject with a therapy for psoriatic arthritis selected from the group consisting of methotrexate, an anti-TNFα inhibitor, ustekinumab, apremilast, and an anti-IHL17 therapy.

5. A method according to claim 4, further comprising determining the quantitative or qualitative level of one or more further biomarkers selected from: Alpha-1-acid glycoprotein 1; Alpha-1-antitrypsin; Insulin-like growth factor-binding protein complex acid labile subunit; Antithrombin; C4b-binding protein alpha chain; Ceruloplasmin; Complement factor B; Clusterin; Platelet basic protein; Extracellular matrix protein 1; Inter-alpha-trypsin inhibitor heavy chain H4; Kininogen-1; Lipopolysaccharide-binding protein; Pigment epithelium-derived factor; Vitamin K-dependent protein C; and Prothrombin.

6. A method according to claim 4, further comprising determining the quantitative or qualitative level of one or more further biomarkers selected from: Gelsolin; Filamin-C; Complement component C9b; Peroxiredoxin-2; Plasma serine protease inhibitor; Adenosine deaminase 2; Pregnancy zone protein; Myomegalin; Apolipoprotein D; Glycocalicin; Afamin; Plasma protease C1 inhibitor; Inter-alpha-trypsin inhibitor heavy chain H3; Insulin-like growth factor-binding protein 3; Galectin-3-binding protein; Alpha-2-HS-glycoprotein chain B; and Antithrombin-III.

7. A method according to claim 2, wherein the determining step (a) comprises determining the quantitative or qualitative level of all of the biomarkers in the blood sample from the subject.

8. A method according to claim 2, wherein the determining step (a) comprises determining the quantitative or qualitative level of each of the biomarkers in the blood sample from the subject.

9. A method according to claim 2, wherein the or each biomarker is a protein having an amino acid sequence selected from any one of SEQ ID NOs: 19-37.

10. A method according to claim 3, wherein the or each biomarker is a protein having an amino acid sequence selected from any one of SEQ ID NOs: 38-55.

11. A method according to claim 4, wherein the blood sample is a serum sample.

12. A method according to claim 1, wherein the method further comprises determining the quantitative or qualitative level of one or more further biomarkers selected from: Alpha-1-antichymotrypsin; Complement C4-B; Coagulation factor XI; Haptoglobin; Haptoglobin-related protein; and Thrombospondin-1.

13. A method according to claim 4, wherein the method further comprises determining the quantitative or qualitative level of one or more further biomarkers selected from: Alpha-1-antichymotrypsin; Complement C4-B; Coagulation factor XI; Haptoglobin; Haptoglobin-related protein; and Thrombospondin-1.

14. A method according to claim 1, wherein the blood sample is a serum sample.

* * * * *

SEQUENCE LISTING

<160> NUMBER OF SEQ ID NOS: 54

<210> SEQ ID NO 1
<211> LENGTH: 11
<212> TYPE: PRT
<213> ORGANISM: Homo sapiens

<400> SEQUENCE: 1

Ala Ser Ser Leu Glu Ser Gly Val Pro Ser Arg
1               5                   10

<210> SEQ ID NO 2
<211> LENGTH: 10
<212> TYPE: PRT
<213> ORGANISM: Homo sapiens

<400> SEQUENCE: 2

Val Ala Ala Gly Ala Phe Gln Gly Leu Arg
1               5                   10

<210> SEQ ID NO 3
<211> LENGTH: 10
<212> TYPE: PRT
<213> ORGANISM: Homo sapiens

<400> SEQUENCE: 3

Ala Asp Leu Ser Gly Ile Thr Gly Ala Arg
1               5                   10

<210> SEQ ID NO 4
<211> LENGTH: 18
<212> TYPE: PRT
<213> ORGANISM: Homo sapiens

<400> SEQUENCE: 4

Thr Leu Asp Leu Gly Glu Asn Gln Leu Glu Thr Leu Pro Pro Asp Leu
1               5                   10                  15

Leu Arg

<210> SEQ ID NO 5
<211> LENGTH: 10
<212> TYPE: PRT
<213> ORGANISM: Homo sapiens

<400> SEQUENCE: 5

Ala Asp Leu Ser Gly Ile Thr Gly Ala Arg
1               5                   10

<210> SEQ ID NO 6
<211> LENGTH: 9
<212> TYPE: PRT
<213> ORGANISM: Homo sapiens

<400> SEQUENCE: 6

Glu Ile Gly Glu Leu Tyr Leu Pro Lys
1               5

<210> SEQ ID NO 7
<211> LENGTH: 11
<212> TYPE: PRT
<213> ORGANISM: Homo sapiens

<400> SEQUENCE: 7

Ile Thr Leu Leu Ser Ala Leu Val Glu Thr Arg
1               5                   10

<210> SEQ ID NO 8
<211> LENGTH: 12
<212> TYPE: PRT
<213> ORGANISM: Homo sapiens

-continued

```
<400> SEQUENCE: 8

Gly Ser Ser Thr Trp Leu Thr Ala Phe Val Leu Lys
1               5                   10

<210> SEQ ID NO 9
<211> LENGTH: 13
<212> TYPE: PRT
<213> ORGANISM: Homo sapiens

<400> SEQUENCE: 9

Gly Leu Glu Glu Glu Leu Gln Phe Ser Leu Gly Ser Lys
1               5                   10

<210> SEQ ID NO 10
<211> LENGTH: 9
<212> TYPE: PRT
<213> ORGANISM: Homo sapiens

<400> SEQUENCE: 10

Asp Ile Tyr Val Asp Leu Asp Met Lys
1               5

<210> SEQ ID NO 11
<211> LENGTH: 9
<212> TYPE: PRT
<213> ORGANISM: Homo sapiens

<400> SEQUENCE: 11

Asp Ser Val Thr Glu Thr Leu Pro Arg
1               5

<210> SEQ ID NO 12
<211> LENGTH: 10
<212> TYPE: PRT
<213> ORGANISM: Homo sapiens

<400> SEQUENCE: 12

Val Thr Ser Ile Gln Asp Trp Val Gln Lys
1               5                   10

<210> SEQ ID NO 13
<211> LENGTH: 9
<212> TYPE: PRT
<213> ORGANISM: Homo sapiens

<400> SEQUENCE: 13

Val Gly Tyr Val Ser Gly Trp Gly Arg
1               5

<210> SEQ ID NO 14
<211> LENGTH: 10
<212> TYPE: PRT
<213> ORGANISM: Homo sapiens

<400> SEQUENCE: 14

Leu Leu Val Val Tyr Pro Trp Thr Gln Arg
1               5                   10

<210> SEQ ID NO 15
<211> LENGTH: 13
<212> TYPE: PRT
<213> ORGANISM: Homo sapiens

<400> SEQUENCE: 15
```

-continued

```
Val Asn Val Asp Glu Val Gly Gly Glu Ala Leu Gly Arg
1               5                   10

<210> SEQ ID NO 16
<211> LENGTH: 8
<212> TYPE: PRT
<213> ORGANISM: Homo sapiens

<400> SEQUENCE: 16

Gly Ser Phe Pro Trp Gln Ala Lys
1               5

<210> SEQ ID NO 17
<211> LENGTH: 12
<212> TYPE: PRT
<213> ORGANISM: Homo sapiens

<400> SEQUENCE: 17

Phe Val Phe Gly Thr Thr Pro Glu Asp Ile Leu Arg
1               5                   10

<210> SEQ ID NO 18
<211> LENGTH: 9
<212> TYPE: PRT
<213> ORGANISM: Homo sapiens

<400> SEQUENCE: 18

Ser Asp Val Val Tyr Thr Asp Trp Lys
1               5

<210> SEQ ID NO 19
<211> LENGTH: 10
<212> TYPE: PRT
<213> ORGANISM: Homo sapiens

<400> SEQUENCE: 19

Ser Val Leu Gly Gln Leu Gly Ile Thr Lys
1               5                   10

<210> SEQ ID NO 20
<211> LENGTH: 9
<212> TYPE: PRT
<213> ORGANISM: Homo sapiens

<400> SEQUENCE: 20

Ser Ile Thr Gly Thr Tyr Asp Leu Lys
1               5

<210> SEQ ID NO 21
<211> LENGTH: 8
<212> TYPE: PRT
<213> ORGANISM: Homo sapiens

<400> SEQUENCE: 21

Leu Glu Tyr Leu Leu Leu Ser Arg
1               5

<210> SEQ ID NO 22
<211> LENGTH: 6
<212> TYPE: PRT
<213> ORGANISM: Homo sapiens

<400> SEQUENCE: 22

Ser Leu Asn Pro Asn Arg
1               5
```

```
<210> SEQ ID NO 23
<211> LENGTH: 12
<212> TYPE: PRT
<213> ORGANISM: Homo sapiens

<400> SEQUENCE: 23

Leu Ser Leu Glu Ile Glu Gln Leu Glu Leu Gln Arg
1               5                   10

<210> SEQ ID NO 24
<211> LENGTH: 12
<212> TYPE: PRT
<213> ORGANISM: Homo sapiens

<400> SEQUENCE: 24

Ala Leu Tyr Leu Gln Tyr Thr Asp Glu Thr Phe Arg
1               5                   10

<210> SEQ ID NO 25
<211> LENGTH: 13
<212> TYPE: PRT
<213> ORGANISM: Homo sapiens

<400> SEQUENCE: 25

Gly Ala Tyr Pro Leu Ser Ile Glu Pro Ile Gly Val Arg
1               5                   10

<210> SEQ ID NO 26
<211> LENGTH: 14
<212> TYPE: PRT
<213> ORGANISM: Homo sapiens

<400> SEQUENCE: 26

Val Ser Glu Ala Asp Ser Ser Asn Ala Asp Trp Val Thr Lys
1               5                   10

<210> SEQ ID NO 27
<211> LENGTH: 10
<212> TYPE: PRT
<213> ORGANISM: Homo sapiens

<400> SEQUENCE: 27

Thr Leu Leu Ser Asn Leu Glu Glu Ala Lys
1               5                   10

<210> SEQ ID NO 28
<211> LENGTH: 10
<212> TYPE: PRT
<213> ORGANISM: Homo sapiens

<400> SEQUENCE: 28

Asn Ile Gln Ser Leu Glu Val Ile Gly Lys
1               5                   10

<210> SEQ ID NO 29
<211> LENGTH: 8
<212> TYPE: PRT
<213> ORGANISM: Homo sapiens

<400> SEQUENCE: 29

Ala Trp Glu Asp Thr Leu Asp Lys
1               5
```

-continued

```
<210> SEQ ID NO 30
<211> LENGTH: 7
<212> TYPE: PRT
<213> ORGANISM: Homo sapiens

<400> SEQUENCE: 30

Ser Ile Gln Asn Asn Val Arg
1               5

<210> SEQ ID NO 31
<211> LENGTH: 8
<212> TYPE: PRT
<213> ORGANISM: Homo sapiens

<400> SEQUENCE: 31

Tyr Phe Ile Asp Phe Val Ala Arg
1               5

<210> SEQ ID NO 32
<211> LENGTH: 11
<212> TYPE: PRT
<213> ORGANISM: Homo sapiens

<400> SEQUENCE: 32

Ile Thr Leu Pro Asp Phe Thr Gly Asp Leu Arg
1               5                   10

<210> SEQ ID NO 33
<211> LENGTH: 9
<212> TYPE: PRT
<213> ORGANISM: Homo sapiens

<400> SEQUENCE: 33

Ser Ser Phe Val Ala Pro Leu Glu Lys
1               5

<210> SEQ ID NO 34
<211> LENGTH: 8
<212> TYPE: PRT
<213> ORGANISM: Homo sapiens

<400> SEQUENCE: 34

Thr Phe Val Leu Asn Phe Ile Lys
1               5

<210> SEQ ID NO 35
<211> LENGTH: 6
<212> TYPE: PRT
<213> ORGANISM: Homo sapiens

<400> SEQUENCE: 35

Ser Gly Trp Glu Gly Arg
1               5

<210> SEQ ID NO 36
<211> LENGTH: 9
<212> TYPE: PRT
<213> ORGANISM: Homo sapiens

<400> SEQUENCE: 36

Glu Thr Trp Thr Ala Asn Val Gly Lys
1               5

<210> SEQ ID NO 37
<211> LENGTH: 15
```

```
<212> TYPE: PRT
<213> ORGANISM: Homo sapiens

<400> SEQUENCE: 37

Glu Val Gln Gly Phe Glu Ser Ala Thr Phe Leu Gly Tyr Phe Lys
1               5                   10                  15

<210> SEQ ID NO 38
<211> LENGTH: 9
<212> TYPE: PRT
<213> ORGANISM: Homo sapiens

<400> SEQUENCE: 38

Asn Asp Asn Asp Thr Phe Thr Val Lys
1               5

<210> SEQ ID NO 39
<211> LENGTH: 11
<212> TYPE: PRT
<213> ORGANISM: Homo sapiens

<400> SEQUENCE: 39

Thr Ser Asn Phe Asn Ala Ala Ile Ser Leu Lys
1               5                   10

<210> SEQ ID NO 40
<211> LENGTH: 11
<212> TYPE: PRT
<213> ORGANISM: Homo sapiens

<400> SEQUENCE: 40

Leu Ser Pro Ile Tyr Asn Leu Val Pro Val Lys
1               5                   10

<210> SEQ ID NO 41
<211> LENGTH: 8
<212> TYPE: PRT
<213> ORGANISM: Homo sapiens

<400> SEQUENCE: 41

Thr Asp Glu Gly Ile Ala Tyr Arg
1               5

<210> SEQ ID NO 42
<211> LENGTH: 8
<212> TYPE: PRT
<213> ORGANISM: Homo sapiens

<400> SEQUENCE: 42

Gln Leu Glu Leu Tyr Leu Pro Lys
1               5

<210> SEQ ID NO 43
<211> LENGTH: 9
<212> TYPE: PRT
<213> ORGANISM: Homo sapiens

<400> SEQUENCE: 43

Ile Gly His Gly Phe Ala Leu Ser Lys
1               5

<210> SEQ ID NO 44
<211> LENGTH: 11
<212> TYPE: PRT
<213> ORGANISM: Homo sapiens
```

```
<400> SEQUENCE: 44

Ser Ser Gly Ser Leu Leu Asn Asn Ala Ile Lys
1               5                   10

<210> SEQ ID NO 45
<211> LENGTH: 7
<212> TYPE: PRT
<213> ORGANISM: Homo sapiens

<400> SEQUENCE: 45

Ile Tyr Phe Leu Glu Glu Arg
1               5

<210> SEQ ID NO 46
<211> LENGTH: 7
<212> TYPE: PRT
<213> ORGANISM: Homo sapiens

<400> SEQUENCE: 46

Val Leu Asn Gln Glu Leu Arg
1               5

<210> SEQ ID NO 47
<211> LENGTH: 10
<212> TYPE: PRT
<213> ORGANISM: Homo sapiens

<400> SEQUENCE: 47

Leu Thr Ser Leu Pro Leu Gly Ala Leu Arg
1               5                   10

<210> SEQ ID NO 48
<211> LENGTH: 7
<212> TYPE: PRT
<213> ORGANISM: Homo sapiens

<400> SEQUENCE: 48

Phe Leu Val Asn Leu Val Lys
1               5

<210> SEQ ID NO 49
<211> LENGTH: 10
<212> TYPE: PRT
<213> ORGANISM: Homo sapiens

<400> SEQUENCE: 49

Leu Leu Asp Ser Leu Pro Ser Asp Thr Arg
1               5                   10

<210> SEQ ID NO 50
<211> LENGTH: 7
<212> TYPE: PRT
<213> ORGANISM: Homo sapiens

<400> SEQUENCE: 50

Ala Leu Asp Leu Ser Leu Lys
1               5

<210> SEQ ID NO 51
<211> LENGTH: 8
<212> TYPE: PRT
<213> ORGANISM: Homo sapiens

<400> SEQUENCE: 51
```

```
Phe Leu Asn Val Leu Ser Pro Arg
1               5

<210> SEQ ID NO 52
<211> LENGTH: 13
<212> TYPE: PRT
<213> ORGANISM: Homo sapiens

<400> SEQUENCE: 52

Ser Asp Leu Ala Val Pro Ser Glu Leu Ala Leu Leu Lys
1               5                   10

<210> SEQ ID NO 53
<211> LENGTH: 6
<212> TYPE: PRT
<213> ORGANISM: Homo sapiens

<400> SEQUENCE: 53

Ala His Tyr Asp Leu Arg
1               5

<210> SEQ ID NO 54
<211> LENGTH: 10
<212> TYPE: PRT
<213> ORGANISM: Homo sapiens

<400> SEQUENCE: 54

Val Gly Asp Thr Leu Asn Leu Asn Leu Arg
1               5                   10
```